(12) United States Patent
Gao et al.

(10) Patent No.: US 8,859,588 B2
(45) Date of Patent: Oct. 14, 2014

(54) SUBSTITUTED N-HETEROARYL BIPYRROLIDINE CARBOXAMIDES, PREPARATION AND THERAPEUTIC USE THEREOF

(71) Applicant: SANOFI, Paris (FR)

(72) Inventors: Zhongli Gao, Flemington, NJ (US); Daniel Hall, Hillsborough, NJ (US); David Stefany, Succasunna, NJ (US)

(73) Assignee: Sanofi, Paris (FR)

( * ) Notice: Subject to any disclaimer, the term of this patent is extended or adjusted under 35 U.S.C. 154(b) by 45 days.

(21) Appl. No.: 13/670,046

(22) Filed: Nov. 6, 2012

(65) Prior Publication Data

US 2013/0065923 A1 Mar. 14, 2013

Related U.S. Application Data

(63) Continuation of application No. PCT/US2011/035844, filed on May 10, 2011.

(60) Provisional application No. 61/333,390, filed on May 11, 2010.

(30) Foreign Application Priority Data

Dec. 24, 2010 (FR) ..................... 10 61240

(51) Int. Cl.
C07D 401/14 (2006.01)
A61K 31/44 (2006.01)
C07D 409/14 (2006.01)
C07D 401/04 (2006.01)
C07D 413/14 (2006.01)
C07D 403/14 (2006.01)
C07D 405/14 (2006.01)

(52) U.S. Cl.
CPC ............ C07D 401/14 (2013.01); C07D 409/14 (2013.01); C07D 401/04 (2013.01); C07D 413/14 (2013.01); C07D 403/14 (2013.01); C07D 405/14 (2013.01)
USPC ........ 514/318; 514/343; 546/193; 546/272.1; 546/279.1

(58) Field of Classification Search
None
See application file for complete search history.

(56) References Cited

U.S. PATENT DOCUMENTS

| 3,960,961 | A  | 6/1976 | Lednicer |
| 7,223,788 | B2 | 5/2007 | Schwink et al. |
| 8,088,808 | B2 | 1/2012 | Czechtizky et al. |
| 8,217,052 | B2 | 7/2012 | Gao et al. |
| 8,222,290 | B2 | 7/2012 | Czechtizky et al. |
| 8,227,481 | B2 | 7/2012 | Gao et al. |
| 8,227,504 | B2 | 7/2012 | Czechtizky et al. |
| 8,252,824 | B2 | 8/2012 | Czechtizky et al. |
| 2010/0173897 | A1 | 7/2010 | Czechtizky et al. |
| 2012/0258979 | A1 | 10/2012 | Gao et al. |

FOREIGN PATENT DOCUMENTS

| EP | 379806 A2 * | 8/1990 |
| EP | 1669350 | 6/2006 |
| WO | WO 2004/037257 | 5/2004 |
| WO | WO 2005/087746 | 9/2005 |
| WO | WO 2005/117865 | 12/2005 |
| WO | WO 2006/047256 | 5/2006 |
| WO | WO 2006/132914 | 12/2006 |
| WO | WO 2007/093364 | 8/2007 |
| WO | WO 2007/133561 | 11/2007 |
| WO | WO 2009/036117 | 3/2009 |
| WO | WO 2009/039431 | 3/2009 |
| WO | WO 2009/052062 | 4/2009 |
| WO | WO 2009/052063 | 4/2009 |
| WO | WO 2009/052065 | 4/2009 |
| WO | WO 2009/052068 | 4/2009 |
| WO | WO 2010/007382 | 1/2010 |
| WO | WO 2010/047956 | 4/2010 |
| WO | WO 2010/065798 | 6/2010 |
| WO | WO 2010/065803 | 6/2010 |

OTHER PUBLICATIONS

U.S. Appl. No. 13/483,503, filed May 30, 2012, Gao et al.
U.S. Appl. No. 13/669,998, filed Nov. 6, 2012, Gao et al.
U.S. Appl. No. 13/670,010, filed Nov. 6, 2012, Gao et al.
U.S. Appl. No. 13/670,026, filed Nov. 6, 2012, Gao et al.
U.S. Appl. No. 13/670,067, filed Nov. 6, 2012, Gao et al.
U.S. Appl. No. 13/670,082, filed Nov. 6, 2012, Gao et al.
U.S. Appl. No. 13/670,111, filed Nov. 6, 2012, Gao et al.

(Continued)

Primary Examiner — Zinna Northington Davis

(57) ABSTRACT

The present disclosure relates to a series of substituted N-heteroaryl bipyrrolidine carboxamides of formula (I).

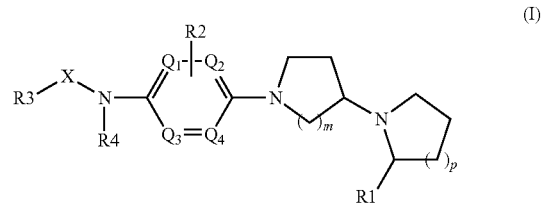

wherein $R_1$, $R_2$, $R_3$, $R_4$, $Q_1$, $Q_2$, $Q_3$, $Q_4$, X, m and p are as described herein. More specifically, the compounds of this invention are modulators of H3 receptors and are, therefore, useful as pharmaceutical agents, especially in the treatment and/or prevention of a variety of diseases modulated by H3 receptors including diseases associated with the central nervous system. Additionally, this disclosure also relates to methods of preparation of substituted N-heteroaryl bipyrrolidine carboxamides of formula (I) and intermediates therefor.

15 Claims, No Drawings

(56) References Cited

OTHER PUBLICATIONS

International Search Report for WO2011/143162 dated Nov. 17, 2011.

Hancock, The Challenge of Drug Discovery of a GPCR Target: Analysis of Preclinical Pharmacology of Histamine H3 Antagonists/ Inverse Agonists, Biochemical Pharmacology, vol. 71, (2006), pp. 1103-1113.

Esbenshade, et al., Histamine H3 Receptor Antagonists: Preclinical Promise for Treating Obesity and Cognitive Disorders, Mol. Interv., (2006), vol. 6, No. 2, pp. 77-88.

Old, et al., A Highly Active Catalyst for Palladium-Catalyzed Cross-Coupling Reactions: Room-Temperature Suzuki Couplings and Amination of Unactivated Aryl Chlorides, J. Am. Chem. Soc., (1998), vol. 120, pp. 9722-9723.

Wolfe, et al., Simple, Efficient Catalyst System for the Palladium-Catalyzed Amination of Aryl Chlorides, Bromides, and Triflates, J. Org. Chem., (2000), vol. 65, pp. 1158-1174.

Van Der Poel, et al., Temporal Patterning of Ultrasonic Distress Calls in the Adult Rat: Effects of Morphine and Benzodiazepines, Pschopharmacology, vol. 97, pp. 147-148, (1989).

Porsalt, et al., Depression: A New Animal Model Sensitive to Antidepressant Treatments, Nature, vol. 266, (1977), pp. 730-732.

Voskresensky, et al., Selective One-Pot N-Monomethylation of 2-Nitroanilines Under Ptc Conditions, Synthetic Communications, vol. 30, No. 19, pp. 3523-3526, (2000).

Cho, et al., Direct and Indirect Reductive Amination of Aldehydes and Ketones With Solid Acid-Activated Sodium Borohydride Under Solvent-Free Conditions, Tetrahedron, vol. 61, (2005). pp. 5725-5734.

Nagumo, et al., Synthesis of (−)-TAN1251A Using 4-Hydroxy-L-Proline as a Chiral Source, Tetrahedron, vol. 58, (2002), pp. 9871-9877.

Stafford, et al., Asymmetric Total Synthesis of (−)-Secodaphniphylline, J. Org. Chem., (1990), vol. 55, pp. 5433-5434.

Boiteau, et al., High Efficiency and Enantioselectivity in the Rh-Catalyzed Conjugate Addition of Arylboronic Acids Using Monodentate Phosphoramidites, J. Org. Chem., vol. 68, pp. 9481-9484, (2003).

Takaya, et al., Rhodium-Catalyzed Asymmetric 1,4-Addition of Aryl- and Alkenylboronic Acids to Enones, J. Am. Chem. Soc., (1998), vol. 120, pp. 5579-5580.

Nguyen, et al., The First General Palladium Catalyst for the Suzuki-Miyaura and Carbonyl Enolate Coupling of Aryl Arenesulfonates, J. Am. Chem. Soc., (2003), vol. 125, pp. 11818-11819.

Denhart, et al., Conformationally Restricted Homotryptamines. Part 5: 3-(Trans-2-Aminomethylcyclopentyl) Indoles as Potent Selective Serotonin Reuptake Inhibitors, Bioorganic & Medicinal Chemistry Letter, vol. 19, (2009), pp. 4031-4033.

Evarts, et al., An Efficient and Convenient Synthesis of Enantiopure 4-(t-Butyldimethylsilyloxy)-cyclohex-2-en-1-one: A Formal Synthesis of (±)-Mesembranol, Tetrahedron Letters, vol. 42, (2001), pp. 3673-3675.

Lott, et al., Trimethylsilyl Iodide as a Peptide Deblocking Agent, J. Chem. Soc., Chem. Commun., (1979), pp. 495-496.

Comins, et al., Pyridine-Derived Triflating Reagents: An Improved Preparation of Vinyl Triflates From Metallo Enolates, Tetrahedron Letters, vol. 33, No. 42, pp. 6299-6302, (1992).

* cited by examiner

SUBSTITUTED N-HETEROARYL BIPYRROLIDINE CARBOXAMIDES, PREPARATION AND THERAPEUTIC USE THEREOF

This application is a continuation of International Application No. PCT/US2011/035844, filed May 10, 2011, which claims the benefit of priority of U.S. Provisional Application No. 61/333,390, filed May 11, 2010, both of which are incorporated herein by reference, and which also claims the benefit of priority of French Application No. 1061240, filed Dec. 24, 2010.

BACKGROUND OF THE INVENTION

1. Field of the Invention

The present invention relates to a series of substituted N-heteroaryl bipyrrolidine carboxamides. The compounds of this invention are modulators of H3 receptors and are, therefore, useful as pharmaceutical agents, especially in the treatment and/or prevention of a variety of diseases modulated by H3 receptors including diseases associated with the central nervous system. Additionally, this invention also relates to methods of preparation of substituted N-heteroaryl bipyrrolidine carboxamides and intermediates therefor.

2. Description of the Background Art

Histamine is a ubiquitous messenger molecule released from mast cells, enterochromaffin-like cells, and neurons. The physiological actions of histamine are mediated by four pharmacologically defined receptors (H1, H2, H3 and H4). All histamine receptors exhibit seven transmembrane domains and are members of the G-protein-coupled receptor superfamily (GPCRs).

The H1 receptor was the first member of the histamine receptor family to be pharmacologically defined, with the development of classical antihistamines (antagonists), such as diphenhydramine and fexofenadine. While antagonism of the H1 receptor of the immune system is commonly used for the treatment of allergic reactions, the H1 receptor is also expressed in various peripheral tissues and the central nervous system (CNS). In the brain, H1 is involved in the control of wakefulness, mood, appetite and hormone secretion.

The H2 receptor is also expressed in the CNS, where it may modulate several processes, including cognition. However, H2 receptor antagonists have primarily been developed to ameliorate gastric ulcers by inhibiting histamine-mediated gastric acid secretion by parietal cells. Classic H2 antagonists include cimetidine, ranitidine, and famotidine.

It should further be noted that H4 receptor function remains poorly defined, but may involve immune regulation and inflammatory processes.

On the other hand, H3 receptors have also been pharmacologically identified in the CNS, heart, lung, and stomach. The H3 receptor differs significantly from other histamine receptors, exhibiting low sequence homology (H1: 30%, H2: 28%, H4: 51%). H3 is a presynaptic autoreceptor on histamine neurons in the brain and a presynaptic heteroreceptor in non-histamine-containing neurons in both the central and peripheral nervous systems. In addition to histamine, H3 also modulates the release and/or synthesis of other neurotransmitters, including acetylcholine, dopamine, norepinepherin and serotonin. Of particular note, presynaptic modulation of histamine release by H3 allows significant regulation of H1 and H2 receptors in the brain. Modulating multiple neurotransmitter signaling pathways, H3 may contribute to varied physiological processes. Indeed, extensive preclinical evidence indicates that H3 plays a role in cognition, sleep-wake cycle and energy homeostasis.

Modulators of H3 function may be useful in the treatment of central nervous system disorders, such as cognitive impairment associated with schizophrenia (CIAS), dementia of Alzheimer Type (DAT), schizophrenia, Alzheimer's disease, attention-deficit hyperactivity disorder, Parkinson's disease, depression, and epilepsy, sleep disorders (narcolepsy and insomnia), cardiovascular disorders (acute myocardial infarction), respiratory disorders (asthma), obesity, and gastrointestinal disorders. See generally, Hancock. Biochem. Pharmacol. 2006 Apr. 14; 71(8):1103-13 and Esbenshade et al. Mol. Interv. 2006 April; 6(2):77-88, 59.

U.S. Pat. No. 7,223,788 discloses a series of compounds, including substituted bis-pyrrolidines, having melanin concentrating hormone (MCH) receptor antagonists. But the compounds disclosed therein are not reported to be active at the H3 receptor site.

Accordingly, one aspect of this invention is to provide a series of substituted N-heteroaryl bipyrrolidine carboxamides as selective H3 receptor ligands for treatment of H3 receptor regulated CNS disorders.

It is another aspect of this invention to provide processes for the preparation of the substituted N-heteroaryl bipyrrolidine carboxamides as disclosed herein.

Other aspects and further scope of the applicability of the present invention will become apparent from the detailed description that follows.

SUMMARY OF THE INVENTION

It has now been found that the compounds of formula (I) are useful as H3 receptor antagonists and/or inverse agonists. Thus in accordance with the practice of this invention there is provided a compound of formula (I):

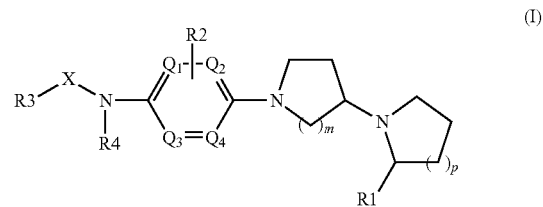

wherein:
m, p=1 or 2;
X is CO or $SO_2$;
$Q_1$ to $Q_4$ are independently CH or N provided that at least one of $Q_1$ to $Q_4$ is N;
$R_1$ is hydrogen, ($C_1$-$C_4$)alkyl, $CF_3$, ($C_1$-$C_4$)alkoxy-($C_1$-$C_4$)alkyl;
$R_2$ is hydrogen, halogen, ($C_1$-$C_4$)alkyl or $CF_3$;
$R_3$ is unsubstituted or substituted aryl selected from naphthyl or phenyl, benzyl, heteroaryl selected from thiophenyl, isoxazolyl, ($C_1$-$C_6$)alkyl, ($C_3$-$C_6$)cycloalkyl, ($C_3$-$C_6$)cycloalkyl containing at least one heteroatom, such as N, O, and S, such as tetrahydropyranyl, piperidinyl, wherein the substituents are selected from the group consisting of halogen, ($C_1$-$C_4$)alkyl and $CH_3CO$; and
$R_4$ is H or ($C_1$-$C_4$)alkyl.

This invention further includes various salts of the compounds of formula (I) including various enantiomers or diastereomers of compounds of formula (I).

In other aspects of this invention there are also provided various pharmaceutical compositions comprising one or more compounds of formula (I) as well as their therapeutic use in alleviating various diseases which are mediated in-part and/or fully by H3 receptors.

DETAILED DESCRIPTION OF THE INVENTION

The terms as used herein have the following meanings:

As used herein, the expression "$(C_1-C_4)$alkyl" includes methyl and ethyl groups, and straight-chained or branched propyl, and butyl groups. Particular alkyl groups are methyl, ethyl, n-propyl, isopropyl and tert-butyl. Derived expressions such as "$(C_1-C_4)$alkoxy", "$(C_1-C_4)$alkoxy$(C_1-C_4)$alkyl", or "hydroxy$(C_1-C_4)$alkyl" are to be construed accordingly.

As used herein, the expression "$(C_1-C_6)$perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$(C_1-C_6)$perfluoroalkoxy", is to be construed accordingly.

"Halogen" or "halo" means chloro, fluoro, bromo, and iodo.

As used herein, "patient" means a warm blooded animal, such as for example rat, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, nitric acid, sulfamic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, propionic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist substantially anhydrous or can be hydrated. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts, and salts formed with suitable organic ligands, e.g. quaternary ammonium salts.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). Similarly, certain compounds of this invention may exist in a mixture of two or more structurally distinct forms that are in rapid equilibrium, commonly known as tautomers. Representative examples of tautomers include keto-enol tautomers, phenol-keto tautomers, nitroso-oxime tautomers, imine-enamine tautomers, etc. It is to be understood that all such isomers and mixtures thereof in any proportion are encompassed within the scope of the present invention.

As used herein, 'R' and 'S' are used as commonly used terms in organic chemistry to denote specific configuration of a chiral center. The term 'R' (rectus) refers to that configuration of a chiral center with a clockwise relationship of group priorities (highest to second lowest) when viewed along the bond toward the lowest priority group. The term 'S' (sinister) refers to that configuration of a chiral center with a counterclockwise relationship of group priorities (highest to second lowest) when viewed along the bond toward the lowest priority group. The priority of groups is based upon sequence rules wherein prioritization is first based on atomic number (in order of decreasing atomic number). A listing and discussion of priorities is contained in *Stereochemistry of Organic Compounds*, Ernest L. Eliel, Samuel H. Wilen and Lewis N. Mander, editors, Wiley-Interscience, John Wiley & Sons, Inc., New York, 1994.

In addition to the (R)-(S) system, the older D-L system may also be used herein to denote absolute configuration, especially with reference to amino acids. In this system a Fischer projection formula is oriented so that the number 1 carbon of the main chain is at the top. The prefix 'D' is used to represent the absolute configuration of the isomer in which the functional (determining) group is on the right side of the carbon at the chiral center and 'L', that of the isomer in which it is on the left.

In a broad sense, the term "substituted" is contemplated to include all permissible substituents of organic compounds. In a few of the specific embodiments as disclosed herein, the term "substituted" means substituted with one or more substituents independently selected from the group consisting of $(C_1-C_6)$alkyl, $(C_2-C_6)$alkenyl, $(C_1-C_6)$perfluoroalkyl, phenyl, hydroxy, —$CO_2H$, an ester, an amide, $(C_1-C_6)$alkoxy, $(C_1-C_6)$thioalkyl, $(C_1-C_6)$perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

"Therapeutically effective amount" means an amount of the compound which is effective in treating the named disease, disorder or condition.

The term "treating" refers to:

(i) preventing a disease, disorder or condition from occurring in a patient that may be predisposed to the disease, disorder and/or condition, but has not yet been diagnosed as having it;

(ii) inhibiting the disease, disorder or condition, i.e., arresting its development; and (iii) relieving the disease, disorder or condition, i.e., causing regression of the disease, disorder and/or condition.

Thus, in accordance with the practice of this invention there is provided a compound of the formula I:

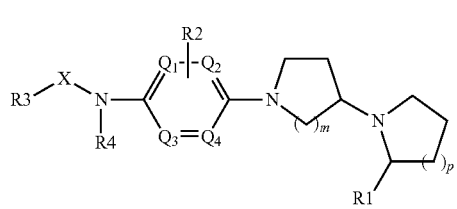

wherein:
m, p=1 or 2;
X is CO or $SO_2$;
$Q_1$ to $Q_4$ are independently CH or N provided that at least one of $Q_1$ to $Q_4$ is N;
$R_1$ is hydrogen, $(C_1-C_4)$alkyl, $CF_3$, $(C_1-C_4)$alkoxy-$(C_1-C_4)$ alkyl;
$R_2$ is hydrogen, halogen, $(C_1-C_4)$alkyl or $CF_3$;
$R_3$ is unsubstituted or substituted aryl selected from naphthyl or phenyl, benzyl, heteroaryl selected from thiophenyl, isoxazolyl, $(C_1-C_6)$alkyl, $(C_3-C_6)$cycloalkyl, $(C_3-C_6)$cycloalkyl containing at least one heteroatom, such as N, O, and S, such as tetrahydropyranyl, piperidinyl, wherein the substituents are selected from the group consisting of halogen, $(C_1-C_4)$alkyl and $CH_3CO$; and
$R_4$ is H or $(C_1-C_4)$alkyl.

This invention further includes various salts of the compounds of formula (I) including various enantiomers or diastereomers of compounds of formula (I). As noted hereinabove and by way of specific examples hereafter all of the salts that can be formed including pharmaceutically acceptable salts are part of this invention. As also noted hereinabove and hereafter all of the conceivable enantiomeric and diastereomeric forms of compounds of formula (I) are part of this invention.

In one of the embodiments, there is provided the compounds of formula (I) wherein
m and p are 1;
X is CO;
$R_1$ is $CH_3$;
$R_2$ is $CH_3$; and
$R_3$ is unsubstituted or substituted naphthyl, phenyl, benzyl, thiophenyl, isoxazolyl, cyclopropyl, cyclohexyl, tetrahydropyranyl or piperidinyl, wherein the substituents are selected from the group consisting of halogen, $(C_1-C_4)$alkyl and $CH_3CO$; and
$R_4$ is H.

In another embodiment of this invention there is also provided a compound of formula (I), wherein
m and p are 1;
X is $SO_2$;
$R_1$ is $CH_3$;
$R_2$ is $CH_3$; and
$R_3$ is unsubstituted or substituted phenyl, cyclopropyl or cyclohexyl, wherein the substituents are selected from the group consisting of halogen, $(C_1-C_4)$alkyl and $CH_3CO$; and
$R_4$ is H.

In both of the above embodiments, the compounds may also include corresponding salts wherever possible including the pharmaceutically acceptable salts thereof.

In another embodiment of this invention the compounds of this invention are having the formula (II):

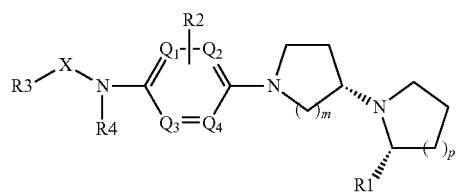

wherein $R_1$, $R_2$, $R_3$, $R_4$, $Q_1$, $Q_2$, $Q_3$, $Q_4$, X, m and p are as defined hereinabove.

In a further aspect of this invention the following compounds encompassed by the scope of this invention without any limitation may be enumerated:
tetrahydro-pyran-4-carboxylic acid [2-methyl-6-((2S,3'S)-2-methyl-[1,3']bipyrrolidinyl-1'-yl)-pyridin-3-yl]-amide;
tetrahydro-pyran-4-carboxylic acid [5-((2S,3'S)-2-methyl-[1,3']bipyrrolidinyl-1'-yl)-pyridin-2-yl]-amide;
naphthalene-1-carboxylic acid [2-methyl-6-((2S,3'S)-2-methyl-[1,3']bipyrrolidinyl-1'-yl)-pyridin-3-yl]-amide;
N-[2-methyl-6-((2S,3'S)-2-methyl-[1,3']bipyrrolidinyl-1'-yl)-pyridin-3-yl]-2-phenyl-acetamide;
cyclohexanesulfonic acid [2-methyl-6-((2S,3'S)-2-methyl-[1,3']bipyrrolidinyl-1'-yl)-pyridin-3-yl]-amide;
3,4-difluoro-N-[2-methyl-6-((2S,3'S)-2-methyl-[1,3']bipyrrolidinyl-1'-yl)-pyridin-3-yl]-benzenesulfonamide;
N-[2-methyl-6-((2S,3'S)-2-methyl-[1,3']bipyrrolidinyl-1'-yl)-pyridin-3-yl]-benzamide;
1-acetyl-piperidine-4-carboxylic acid [2-methyl-6-((2S,3'R)-2-methyl-[1,3']bipyrrolidinyl-1'-yl)-pyridin-3-yl]-amide;
5-fluoro-2-methyl-N-[2-methyl-6-((2S,3'R)-2-methyl-[1,3']bipyrrolidinyl-1'-yl)-pyridin-3-yl]-benzamide;
thiophene-2-carboxylic acid [2-methyl-6-((2S,3'R)-2-methyl-[1,3']bipyrrolidinyl-1'-yl)-pyridin-3-yl]-amide;
3,5-dimethyl-isoxazole-4-carboxylic acid [2-methyl-6-((2S,3'R)-2-methyl-[1,3']bipyrrolidinyl-1'-yl)-pyridin-3-yl]-amide;
4-fluoro-N-[2-methyl-6-((2S,3'R)-2-methyl-[1,3']bipyrrolidinyl-1'-yl)-pyridin-3-yl]-benzenesulfonamide; and
cyclopropanesulfonic acid [2-methyl-6-((2S,3'R)-2-methyl-[1,3']bipyrrolidinyl-1'-yl)-pyridin-3-yl]-amide.

All of the above compounds may also include corresponding salts wherever possible including the pharmaceutically acceptable salts thereof.

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature and as further described herein. For instance, see R. C. Larock, "Comprehensive Organic Transformations," VCH publishers, 1989.

It is also well known that in various organic reactions it may be necessary to protect reactive functional groups, such as for example, amino groups, to avoid their unwanted participation in the reactions. Conventional protecting groups may be used in accordance with standard practice and known to one of skilled in the art, for example, see T. W. Greene and P. G. M. Wuts in "Protective Groups in Organic Chemistry"

John Wiley and Sons, Inc., 1991. For example, suitable amine protecting groups include without any limitation sulfonyl (e.g., tosyl), acyl (e.g., benzyloxycarbonyl or t-butoxycarbonyl) and arylalkyl (e.g., benzyl), which may be removed subsequently by hydrolysis or hydrogenation as appropriate. Other suitable amine protecting groups include trifluoroacetyl [—C(=O)CF$_3$] which may be removed by base catalyzed hydrolysis, or a solid phase resin bound benzyl group, such as a Merrifield resin bound 2,6-dimethoxybenzyl group (Ellman linker) or a 2,6-dimethoxy-4-[2-(polystyrylmethoxy)ethoxy]benzyl, which may be removed by acid catalyzed hydrolysis, for example with TFA.

More specifically, the compounds disclosed herein and various precursors used therefor can be synthesized according to the following procedures of Schemes 1-4, wherein $R_1$, $R_2$, $R_3$, $R_4$, $Q_1$, $Q_2$, $Q_3$, $Q_4$, X, m and p are as defined for Formula I unless otherwise indicated.

Scheme 1 illustrates preparation of enantiomerically pure isomers of the [1,3']pyrrolidinyl-pyrrolidine of formula (5), wherein R is as defined herein.

In step 1, Scheme 1, suitably protected (for example boc) pyrrolidine alcohol of formula (1) is treated with p-toluene sulfonyl chloride to form intermediate of formula (2). This reaction can be carried out using any of the procedures known to one skilled in the art, such as for example, carrying out the reaction in the presence of a suitable base such as triethylamine and DMAP in a suitable organic solvent. Suitable solvents include an aprotic solvent such as dichloromethane. In general, the reaction is carried out at sub-ambient or ambient temperature conditions, however, super-ambient temperature conditions may be employed in certain situations.

ence of solvents such as acetonitrile or butanone at ambient to super-ambient temperature conditions. However, it should be noted that any other base or in some instances acid or another reagent that would bring about such condensation reaction can also be used in this reaction step.

In step 3, Scheme 1, the intermediate of formula (4) is then reacted with an acid, such as hydrochloric acid in a suitable solvent, such as dioxane, to form the desired stereospecific isomer of intermediate of formula (5). It has now been found that the intermediates of formula (5) can be readily formed in accordance with the process of this invention with high enantiomeric purity, specific details of which are provided hereinbelow by way of various examples. In general, the enantiomeric purity can be determined by chiral HPLC.

Scheme 2 illustrates the preparation of amino-hetero-aryl-pyrrolidinyl-pyrrolidine intermediate of formula (8a) and (8b), wherein $R_1$ and $R_2$ are as defined herein.

In step 1, Scheme 2, nitro-hetero-aryl compound of formula (6), wherein Z is a suitable leaving group, such as Cl, F, Br, or triflate (OTf) is condensed with the intermediate of formula (5) in order to form an intermediate of formula (7). Such condensation reactions can again be carried out using any of the procedures known to one skilled in the art. For example, such condensation reaction can be carried out in a polar solvent such as DMSO, or in an aprotic solvent, such as acetonitrile, in the presence of a base such as potassium carbonate at ambient to super-ambient temperature conditions.

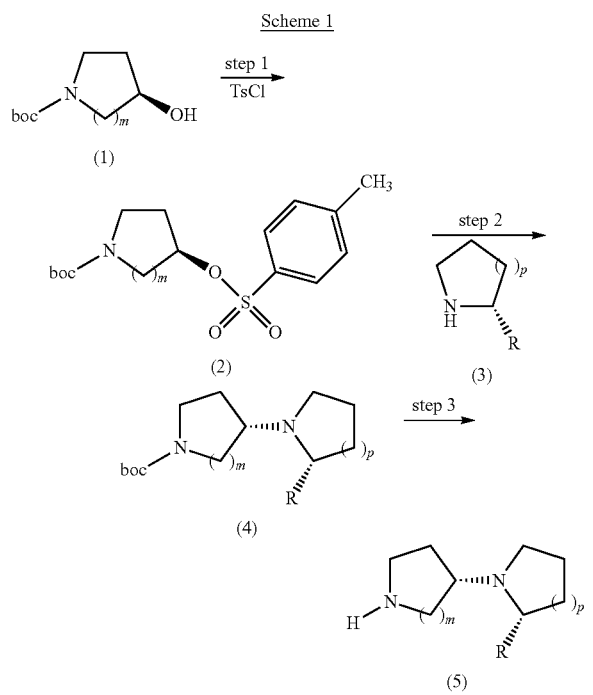

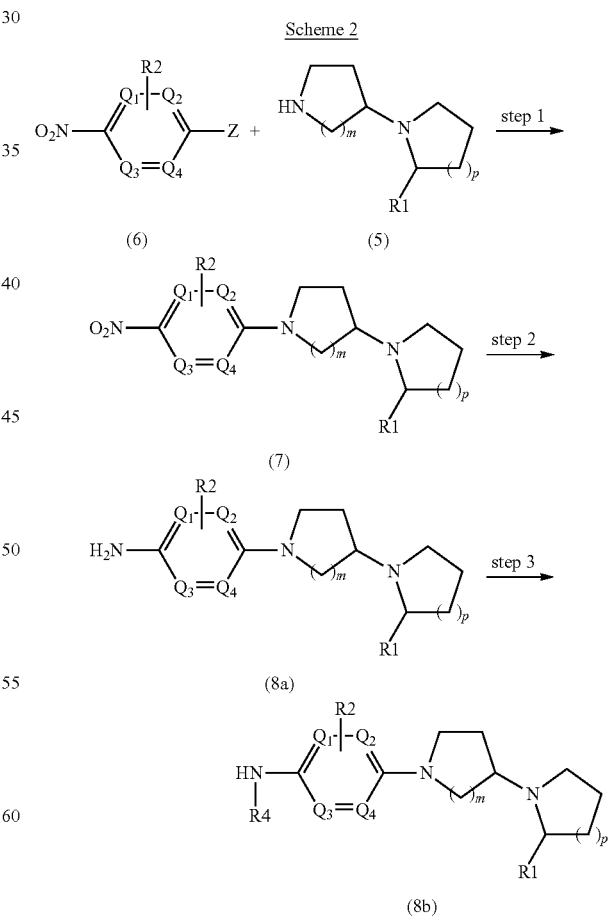

In step 2, Scheme 1, the intermediate of formula (2) is condensed with a desired pyrrolidine of formula (3). Again, such condensation reactions can be carried out using any of the procedures known to one skilled in the art in order to obtain the intermediate of formula (4). Typically, such condensation reactions are carried out in the presence of a base such as potassium carbonate or cesium carbonate in the pres- In step 2, Scheme 2, intermediate of formula (7) is reduced by hydrogenation or by other known reductive chemical methods, such as using tin dichloride in hydrochloric acid or acetic acid or trifluoro-acetic acid, to form the key intermediate (8a). In Step 3, Scheme 2, the amino heteroaryl intermediate of (8a) can be alkylated using the known process, such as N-alkylation (see reference: S. Voskresensky, M. Makosza, *Synth Commun.*, 2000, 30 (19),3523) or reductive amination (see reference: B. T. Cho, S. K Kang, *Tetrahedron*, 2005, 61 (24), 5725), to form the mono-alkylated amino heteroaryl of formula (8b).

Scheme 3 illustrates the preparation of compounds of formula (I) of this invention wherein X=CO using either Method A or Method B depending upon the availability of desired carboxylic acid of formula (9) either in the form of acid itself or its acid chloride. Similar methods can be employed for the preparation of compounds of formula (I) of this invention wherein X=SO₂ using the corresponding sulfonic acid or sulfonyl chloride.

In Method A, Scheme 3, the acid chloride of formula (9) can be reacted with the intermediate (8a) or (8b) using any of the conditions known to one skilled in the art. Typically, such conditions include without any limitations reaction of the acid chloride with the intermediate of formula (8a) or (8b) in a suitable organic solvent such as for example dichloromethane in the presence of a suitable base such as pyridine. Such reactions are generally carried out at sub-ambient temperature conditions, for example around 0° C., however ambient to super-ambient temperature conditions may also be suitable in certain situations depending upon the nature of the acid chloride and the intermediate (8a) or (8b).

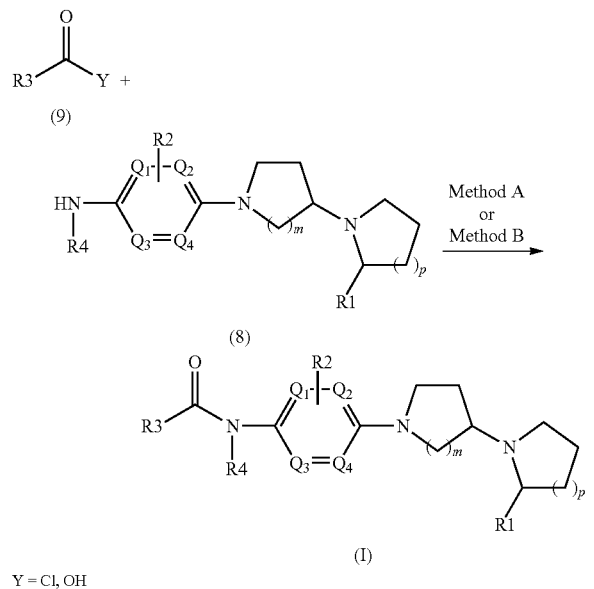

Similarly, in Method B, Scheme 3, the carboxylic acid of formula (9) can be reacted with the intermediate of formula (8a) or (8b) under various reaction conditions known to one skilled in the art. For instance, the acid of formula (9) is reacted with intermediate of formula (8a) or (8b) at sub-ambient temperature conditions in the presence of suitable reagents such as for example a mixture of N-methylmorpholine, 1-hydroxybenzotriazole and EDC HCl, or other suitable peptide coupling reagents, such as TPTU, HOBt in the presence of iPr2NEt, in DCM and/or DMF.

Scheme 4 illustrates the preparation of the compounds of the formula (I) in an alternative process. The acid or acid chloride of the formula (9) is coupled with the commercially available amino-hetero-aryl compound of the formula (10), or its mono-alkylated analog based on the procedures in step 3, Scheme 2, to form amides of the formula (11) by the conditions described in Scheme 3. Then, in step 2, Scheme 4, the compound of formula (11) can be condensed with the intermediate of the formula (5) under the aryl amination conditions known to one skilled in the art, such as catalyzed by Pd(0) with a proper ligand similar to the procedures reported in the literature (D. W. Old, J. P. Wolfe, S. L. Buchwald, *J. Am. Chem. Soc.*, 1998, 120, 9722-9723; J. P. Wolfe, H. Tomori, J. P. Sadighi, J. Yin, and S. L. Buchwald, *J. Org. Chem.*, 2000, 65, 1158-1174 and the reference cited therein), to form the desired compounds of the formula (I) of this invention.

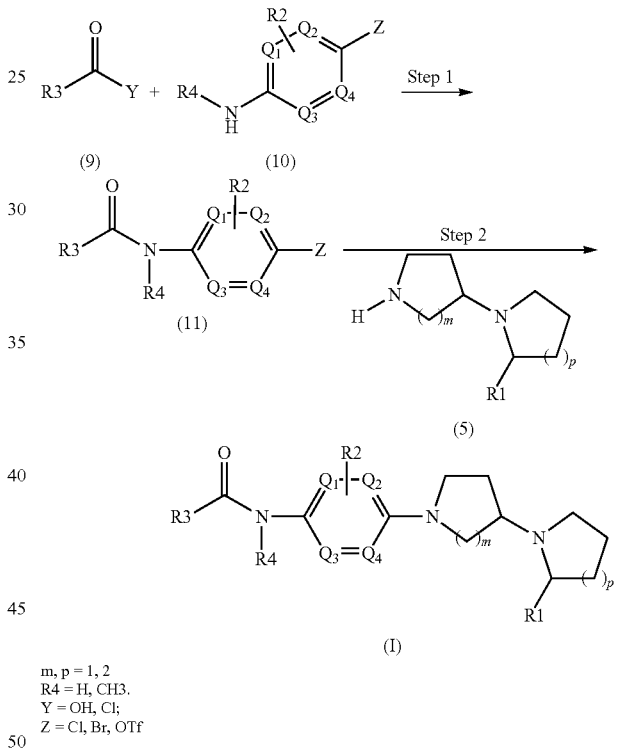

m, p = 1, 2
R4 = H, CH3.
Y = OH, Cl;
Z = Cl, Br, OTf

As already noted hereinabove, the compounds of this invention can readily be converted into salts. More particularly, the compounds of the present invention are basic, and as such compounds of this invention are useful in the form of a free base or in the form of a pharmaceutically acceptable acid addition salt thereof. Acid addition salts may be a more convenient form for use; and, in practice, use of the salt form inherently amounts to use of the free base form. The acids which can be used to prepare the acid addition salts include preferably those which produce, when combined with the free base, pharmaceutically acceptable salts, that is, salts whose anions are non-toxic to the patient in pharmaceutical doses of the salts, so that the beneficial inhibitory effects inherent in the free base are not vitiated by side effects ascribable to the anions. Although pharmaceutically acceptable salts of said basic compound is preferred, all acid addition salts are useful as sources of the free base form even if the particular salt, per se, is desired only as an intermediate product as, for example, when the salt is formed only for purposes of purification, and identification, or when it is used as intermediate in preparing a pharmaceutically acceptable salt by ion exchange procedures.

In another aspect of this embodiment, a specific disease, a disorder or a condition that can be prevented and/or treated with the compound of this invention include, without any limitation the following: sleep-related disorders (specific examples include without any limitation narcolepsy, attentional deficits, circadian rhythm sleep disorders, obstructive sleep apnea, periodic limb movement and restless leg syndrome, excessive sleepiness and drowsiness due to medication side-effect, etc.), neurological disorders (specific examples that may be enumerated include but not limited to dementia, Alzheimer's disease, multiple sclerosis, epilepsy and neuropathic pain), neuropsychological and cognitive disorders (a few of the specific examples include without any limitation include schizophrenia, attention deficit/hyperactivity disorder, Alzheimer's disease, depression, seasonal affective disorder, and cognitive impairment). Certain of the disorders also include cognitive impairment associated with schizophrenia (CIAS), anxiety disorders such as generalized anxiety, panic disorder and post-traumatic stress disorder, and major depressive disorder. Other disorders include dementia of Alzheimer type (DAT), cognitive deficits related to neurological diseases such as Alzheimer, Parkinson, Huntington, age related cognitive impairment, mild cognitive impairment, vascular dementia, Lewis Body dementia and any other cognition associated to cognitive deficits.

As described hereinbelow by way of specific examples, the compounds of formula (I) bind to the H3 receptors and demonstrate inverse agonism versus H3 functional activity. Therefore, the compounds of this invention may have utility in the treatment of diseases or conditions ameliorated with H3 receptor ligands. More specifically, the compounds of the present invention are H3 receptor ligands that modulate function of the H3 receptor by antagonizing the activity of the receptor. Further, the compounds of this invention may be inverse agonists that inhibit the basal activity of the receptor or they may be antagonists that completely block the action of receptor-activating agonists. Additionally, the compounds of this invention may also be partial agonists that partially block or partially activate the H3 receptor or they may be agonists that activate the receptor. Thus the compounds of this invention may act differentially as antagonists, inverse agonists and/or partial agonists depending on functional output, histamine tone and or tissue context. Accordingly, the differential activities of these compounds may allow for utility to ameliorate multiple disease states as specifically enumerated above.

Thus in one aspect of this invention there is provided a method of treating a disease in a patient, said disease selected from the group consisting of sleep related disorder, dementia, Alzheimer's disease, multiple sclerosis, cognitive disorder, attention deficit hyperactivity disorder and depression, comprising administering to said patient a therapeutically effective amount of a compound of formula (I).

One of skill in the art readily appreciates that the pathologies and disease states expressly stated herein are not intended to be limiting rather to illustrate the efficacy of the compounds of the present invention. Thus it is to be understood that the compounds of this invention may be used to treat any disease caused by the effects of H3 receptors. That is, as noted above, the compounds of the present invention are modulators of H3 receptors and may be effectively administered to ameliorate any disease state which is mediated all or in part by H3 receptors.

All of the various embodiments of the compounds of this invention as disclosed herein can be used in the method of treating various disease states as described herein. As stated herein, the compounds used in the method of this invention are capable of inhibiting the effects of H3 receptor and thereby alleviating the effects and/or conditions caused due to the activity of H3.

In another embodiment of the method of this invention, the compounds of this invention can be administered by any of the methods known in the art. Specifically, the compounds of this invention can be administered by oral, intramuscular, subcutaneous, rectal, intratracheal, intranasal, intraperitoneal or topical route.

In another embodiment of this invention the compounds of formulae (I) or (II) of this invention or a pharmaceutically acceptable salt, an enantiomer, or a diastereomer thereof can be used to prepare medicaments and/or pharmaceutical compositions which can be used to inhibiting and/or modulating the effects of H3 receptor and thereby alleviating the effects and/or diseases and/or conditions caused due to the activity of H3. Specific diseases and/or conditions are those which are specifically enumerated as herein. Accordingly, the medicaments produced from the compounds of formulae (I) or (II) of this invention can be used to treat a patient suffering from any of the diseases that are believed to be caused due to the aforementioned effects of H3 receptors. Even more specifically, the compounds of formulae (I) or (II) of this invention can be used to treat various disease states as enumerated herein.

Finally, in yet another embodiment of this invention, there is also provided a pharmaceutical composition comprising a pharmaceutically acceptable carrier and a compound of formula (I), including enantiomers, stereoisomers, and tautomers of said compound and pharmaceutically acceptable salts, solvates or derivatives thereof, with said compound having the general structure shown in formula I as described herein.

As described herein, the pharmaceutical compositions of this invention feature H3 inhibitory activity and thus are useful in treating any disease, condition or a disorder caused due to the effects of H3 in a patient. Again, as described above, all of the preferred embodiments of the compounds of this invention as disclosed herein can be used in preparing the pharmaceutical compositions as described herein.

Preferably the pharmaceutical compositions of this invention are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The pharmaceutical compositions of this invention can be administered by any of the methods known in the art. In general, the pharmaceutical compositions of this invention can be administered by oral, intramuscular, subcutaneous, rectal, intratracheal, intranasal, intraperitoneal or topical route. The preferred administrations of the pharmaceutical composition of this invention are by oral and intranasal routes. Any of the known methods to administer pharmaceutical compositions by an oral or an intranasal route can be used to administer the composition of this invention.

In the treatment of various disease states as described herein, a suitable dosage level is about 0.01 to 250 mg/kg per day, preferably about 0.05 to 100 mg/kg per day, and especially about 0.05 to 20 mg/kg per day. The compounds may be administered on a regimen of 1 to 4 times per day.

This invention is further illustrated by the following examples which are provided for illustration purposes and in no way limit the scope of the present invention.

Examples

General

As used in the examples and preparations that follow, the terms used therein shall have the meanings indicated: "kg" refers to kilograms, "g" refers to grams, "mg" refers to milligrams, "μg" refers to micrograms, "mol" refers to moles, "mmol" refers to millimoles, "μmole" refers to micromoles, "nmole" refers to nanomoles, "L" refers to liters, "mL" or "ml" refers to milliliters, "μL" refers to microliters, "gal" refers to gallons, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "abs." refers to absolute, "conc." refers to concentrated, "c" refers to concentration in g/mL, "DMSO" refers to dimethyl sulfoxide, "DMF" refers to N,N-dimethylformamide, "CDI" refers to 1,1'-carbonyldiimidazole, "DCM" or "$CH_2Cl_2$" refers to dichloromethane, "DCE" refers to 1,2-dichloroethane, "HCl" refers to hydrochloric acid, "EtOAc" refers to ethyl acetate, "PBS" refers to Phosphate Buffered Saline, "PEG" refers to polyethylene glycol, "MeOH" refers to methanol, "$MeNH_2$" refers to methyl amine, "$N_2$" refers to nitrogen gas, "iPrOH" refers to isopropyl alcohol, "$Et_2O$" refers to ethyl ether, "LAH" refers to lithium aluminum hydride, "heptane" refers to n-heptane, "$PdCl_2(dppf)_2$" refers to 1,1'-bis(diphenylphosphino)ferrocene-palladium (II) dichloride DCM complex, "HBTU" refers to 2-(1H-benzotriazol-1yl)-1,1,3,3-tetramethyluronium hexafluorophosphate, "CAS xxx-xx-x" refers to Chemical Abstract Service registration number; "BINAP" refers to 2,2'-bis(diphenylphosphino)-1,1'-binaphthyl; "LDA" refers to lithium diisopropylamide; "DABCO" refers to 1,4-diazabicyclo[2.2.2]octane; "$NaBH(OAc)_3$" refers to sodium triacetoxyborohydride; "DCE" refers to 1,2-dichloroethane; "DIBAL or DIBAL-H" refers to diisobutylaluminium hydride; "DIEA" refers to N,N-diisopropylethylamine; "DMAP" refers to 4-dimethylaminopyridine; "eq. or equiv." refers to equivalent; "$Et_3N$" refers to triethylamine; "HOBT or HOBt" refers to 1-hydroxybenzotriazole; "EDC" refers to ethyl-(3-dimethylamino-propyl)-carbodiimide; "TPTU" refers to [dimethylamino-(2-oxo-2H-pyridin-1-yloxy)-methylene]-dimethyl-ammonium tetrafluoro borate; "HATU" refers to 2-(1H-7-azabenzotriazol-1-yl)-1,1,3,3-tetramethyl uronium hexafluorophosphate methanaminium; "HMPA" refers to hexamethylphosphoramide; "HOAc" refers to acetic acid; "$Pd_2(dba)_3$" refers to tris(dibenzylideneacetone)dipalladium; "$Pd(PPh_3)_4$" refers tetrakis(triphenylphosphine)palladium (0); "SM" refers to starting material; "TBAF" refers to tetrabutylammonium fluoride; "CsF" refers to cesium fluoride, "MeI" refers to methyl iodide, "AcN," "MeCN" or "$CH_3CN$" refers to acetonitrile, "TFA" refers to trifluoroacetic acid, "THF" refers to tetrahydrofuran, "NMP" refers to 1-methyl-2-pyrrolidinone, "$H_2O$" refers to water, "BOC" refers to t-butyloxycarbonyl, "brine" refers to a saturated aqueous sodium chloride solution, "M" refers to molar, "mM" refers to millimolar, "μM" refers to micromolar, "nM" refers to nanomolar, "N" refers to normal, "TLC" refers to thin layer chromatography, "HPLC" refers to high performance liquid chromatography, "HRMS" refers to high resolution mass spectrum, "μCi" refers to microcuries, "i.p." refers to intraperitoneally, "i.v." refers to intravenously, anhyd=anhydrous; aq=aqueous; min=minute; hr=hour; d=day; sat.=saturated; s=singlet, d=doublet; t=triplet; q=quartet; m=multiplet; dd=doublet of doublets; br=broad; LC=liquid chromatograph; MS=mass spectrograph; ESI/MS=electrospray ionization/mass spectrograph; RT=retention time; M=molecular ion, "~"=approximately.

Reactions generally are run under a nitrogen atmosphere. Solvents are dried over magnesium sulfate and are evaporated under vacuum on a rotary evaporator. TLC analyses are performed with EM Science silica gel 60 F254 plates with visualization by UV irradiation. Flash chromatography is performed using Alltech prepacked silica gel cartridges. The $^1$H NMR spectra are run at 300 MHz on a Gemini 300 or Varian Mercury 300 spectrometer with an ASW 5 mm probe, and usually recorded at ambient temperature in a deuterated solvent, such as $D_2O$, DMSO-$D_6$ or $CDCl_3$ unless otherwise noted. Chemical shifts values (δ) are indicated in parts per million (ppm) with reference to tetramethylsilane (TMS) as the internal standard.

High Pressure Liquid Chromatography-Mass Spectrometry (LCMS) experiments to determine retention times ($R_T$) and associated mass ions are performed using one of the following methods:

Mass Spectra (MS) are recorded using a Micromass mass spectrometer. Generally, the method used was positive electro-spray ionization, scanning mass m/z from 100 to 1000. Liquid chromatography was performed on a Hewlett Packard 1100 Series Binary Pump & Degasser; Auxiliary detectors used were: Hewlett Packard 1100 Series UV detector, wavelength=220 nm and Sedere SEDEX 75 Evaporative Light Scattering (ELS) detector temperature=46° C., $N_2$ pressure=4 bar.

LCT: Grad (AcN+0.05% TFA):($H_2O$+0.05% TFA)=5:95 (0 min) to 95:5 (2.5 min) to 95:5 (3 min). Column: YMC Jsphere 33×2 4 μM, 1 ml/min MUX: Column: YMC Jsphere 33×2, 1 ml/min
Grad (AcN-F0.05% TFA):(H2O+0.05% TFA)=5:95 (0 min) to 95:5 (3.4 min) to 95:5 (4.4 min).

LCT2: YMC Jsphere 33×2 4 μM, (AcN+0.05% TFA):(H2O+0.05% TFA)=5:95 (0 min) to 95:5 (3.4 min) to 95:5 (4.4 min)

QU: YMC Jsphere 33×2 1 ml/min, (AcN-F0.08% formic acid):(H2O+0.1% formic acid)=5:95 (0 min) to 95:5 (2.5 min) to 95:5 (3.0 min)

The following examples describe the procedures used for the preparation of various starting materials employed in the preparation of the compounds of this invention.

INTERMEDIATES

Intermediate (i)

(R)-3-(Toluene-4-sulfonyloxy)-pyrrolidine-1-carboxylic acid tert-butyl ester

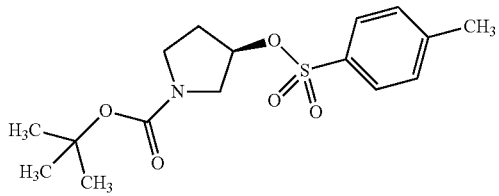 [SMILES: Cc1ccc(S(=O)(=O)O[C@@H]2CCN(C(=O)OC(C)(C)C)C2)cc1]

To a 2 L round-bottom flask equipped with a mechanical stirring rod and a 250 mL addition funnel was added p-tosyl chloride (58 g, 305 mmol, 1.5 eq) and 600 mL of anhydrous DCM. The solution was cooled with ice-water bath. $Et_3N$ (65 ml) and DMAP (2.65 g) were added. A solution of (3R)-(−)-N-Boc-hydroxy pyrrolidine (38 g, 203 mmol, 1.0 eq) in 200 mL of DCM was added slowly. The reaction mixture was allowed to stir at room temperature over night. TLC showed completion of the reaction. The product had an $R_f$ value of 0.3 in DCM. The reaction was cooled by ice-water bath. Polymer-supported trisamine (32 g) was added and stirred for 30 min. Trisamine bead was filtered and rinsed with 300~400 ml of DCM. The organic solution was washed with 200 mL of $H_3PO_4$ (1M) solution twice, followed by saturated $NaHCO_3$ solution (200 ml), and brine (200 ml). The organic phase was dried over $K_2CO_3$. After concentration, the crude product was purified by a 750 g silica gel cartridge (DCM to 5% MeOH in DCM) to afford 52 g (75% yield) of the title compound as a beige oil.

MS: 363 (M+Na+); TLC (DCM) Rf=0.3.
$^1$H NMR (CDCl$_3$, 300 MHz), δ (ppm): 7.80 (d, 9.0 Hz, 2H), 7.35 (d, 7.8 Hz, 2H), 5.04 (bs, 1H), 3.45 (m, 4H), 2.46 (bs, 3H), 2.05 (m, 2H), 1.43 (s, 9H).

Intermediate (ii)

(S)-3-(Toluene-4-sulfonyloxy)-pyrrolidine-1-carboxylic acid tert-butyl ester

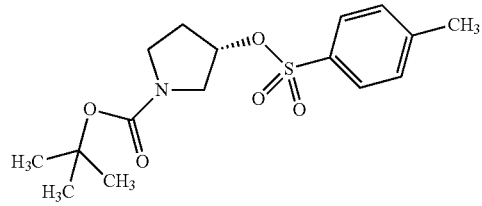 [SMILES: Cc1ccc(S(=O)(=O)O[C@H]2CCN(C(=O)OC(C)(C)C)C2)cc1]

A round bottom flask was charged with 80 mL of anhydrous DCM. The solvent was evacuated and purged with nitrogen. To this solvent was added (3S)-1-BOC-3-pyrrolidinol (obtained from Astatech), (16.32 g, 33.8 mmol), DMAP (0.4 g). The solution was cooled to an ice-water bath. To this cold solution was added a solution of p-toluene-sulfonyl chloride (9.67 g, 50.87 mmol, 1.5 equiv.) in 20 mL of DCM. The ice-water bath was removed and the solution was stirred under nitrogen overnight. TLC (5% MeOH in DCM for SM, I2 visualization; DCM for product, UV) showed the completion of the reaction. The reaction was quenched by addition of polymer-supported amine (4.5 g), stirred 30 min. 50 mL of DCM was added and filtered. The filtration pad was washed with DCM. The organic was washed with $H_3PO_4$ (1M, 2×50 mL), followed by $NaHCO_3$ (50 mL), brine (50 mL), dried ($K_2CO_3$), filtered and concentrated to a liquid. This was purified on a 110 g silica gel column on Analogix using 0-2% MeOH in DCM to obtain pure product, 8.82 g (77% yield).

TLC (DCM) Rf=0.3. LC: Rt=3.55 min., 100% pure based on total ion, MS: 363 (M+Na); 342, 327, 286 (base).
$^1$H NMR (300 MHz, CDCl$_3$), δ (ppm): 7.81 (d, 8.7 Hz, 2H), 7.37 (d, 8.7 Hz, 2H), 5.04 (bs, 1H), 3.45 (m, 4H), 2.46 (s, 3H), 1.44 (s, 9H).

Intermediate (iii)

(2S,3'S)-2-Methyl-[1,3']bipyrrolidinyl-1'-carboxylic acid tert-butyl ester

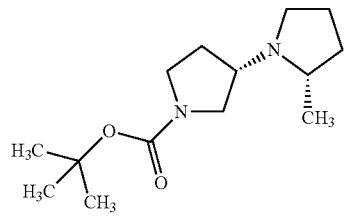 [SMILES: C[C@H]1CCCN1[C@H]1CCN(C(=O)OC(C)(C)C)C1]

The tosylate (52 g, 0.15 mol, 1.0 eq), (2S)-2-methylpyrrolidine (25.2 g, 0.3 mol, 2.0 eq), anhydrous $CH_3CN$ (500 ml), and dry $K_2CO_3$ powder (50 g, 36 mmol, 2.4 eq) were added to a 2 L round-bottom flask equipped with a mechanical stirrer and a reflux condenser. The resulting suspension was stirred at 75° C. for 20 h. The heating block was set at 88° C.

LC/MS showed a trivial amount of starting material at m/z 363. The reaction mixture was concentrated in vacuo. The residue was partitioned between 200 mL of water and 400 mL of DCM. The aqueous layer was washed with 50 mL of DCM twice. The organic extracts were combined and washed with 150 mL of saturated $NaHCO_3$ solution, 150 mL of brine, and dried over $K_2CO_3$. The crude was purified by silica gel column, eluted with 5-10% MeOH in DCM. The product still had weak UV absorption at 254 nm and 280 nm. A pale yellow oil was obtained. Yield: 24.5 g (64%).

LCMS: $R_T$=1.27 min., MS: 255 (M+H).

$^1$H NMR (300 MHz, $CDCl_3$), δ (ppm): 3.15 (m, 2H), 3.3 (m, 3H), 2.97 (m, 1H), 2.71 (m, 1H), 2.47 (m, 1H), 1.98 (m, 2H), 1.96-1.67 (m, 4H), 1.46 (s, 9H), 1.06 (d, 6.2 Hz, 3H).

Intermediate (iv)

(2R,3'S)-2-Methyl-[1,3']bipyrrolidinyl-1'-carboxylic acid tert-butyl ester

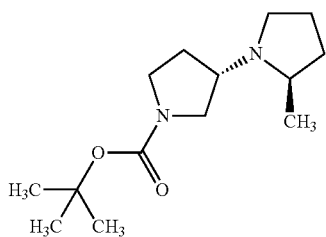 [SMILES: C[C@@H]1CCCN1[C@H]1CCN(C(=O)OC(C)(C)C)C1]

The title compound was prepared in a manner substantially the same as intermediate (2R,3'S)-2-Methyl-[1,3']bipyrrolidinyl-1'-carboxylic acid tert-butyl ester by condensing 3-(3R)-(toluene-4-sulfonyloxy)-pyrrolidine-1-carboxylic acid tert-butyl ester with R-(−)-2-methylpiperindine (obtained from Advanced Asymmetrics). LCMS:

$R_T$=1.05 min, MS: 255 (M+H).

$^1$H NMR (300 MHz, $CDCl_3$), δ (ppm): 3.30 (m, 1H), 3.14 (bs, 2H), 2.91 (m, 1H), 2.75 (m, 1H), 2.51 (m, 1H), 2.07-1.69 (m, 6H), 1.46 (s, 9H), 1.10 (d, 6.0 Hz, 3H).

Intermediate (v)

(2S,3'R)-2-Methyl-[1,3']bipyrrolidinyl-1'-carboxylic acid tert-butyl ester

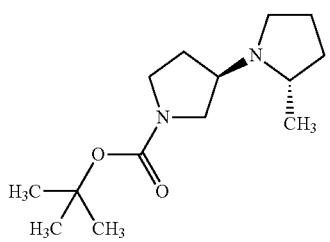 [SMILES: C[C@H]1CCCN1[C@@H]1CCN(C(=O)OC(C)(C)C)C1]

A suspension of 3-(3S)-(Toluene-4-sulfonyloxy)-pyrrolidine-1-carboxylic acid tert-butyl ester (4.51 g, 13.2 mmol), (S)-(+)-2-methylpyrrolidine (1.35 g, 15.84 mmol), and $K_2CO_3$ (4.01 g, 29.04 mmol) in acetonitrile (44 mL) was heated to 80° C. for 20 h and then added additional (S)-(+)-2-Methylpyrrolidine (834 mg, 9.79 mmol), and continued heating for 20 h. Removed from heating and concentrated to provide a residue which was taken up with $H_2O$ (100 mL) and extracted with $CH_2Cl_2$ (2×100 mL). Dried the organics over $K_2CO_3$, filtered and concentrated to provide a crude oil which was purified by flash column chromatography (0 to 5% MeOH/$CH_2Cl_2$) to provide 2.51 g (75% yield) of the title compound as a solid.

Intermediate (vi)

(2R,3'R)-2-Methyl-[1,3']bipyrrolidinyl-1'-carboxylic acid tert-butyl ester

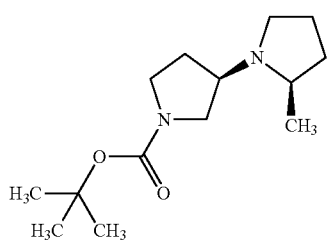 [SMILES: C[C@@H]1CCCN1[C@@H]1CCN(C(=O)OC(C)(C)C)C1]

The title compound was prepared in a manner substantially the same as intermediate (2R,3'S)-2-Methyl-[1,3']bipyrrolidinyl-1'-carboxylic acid tert-butyl ester by condensing 3-(3S)-(toluene-4-sulfonyloxy)-pyrrolidine-1-carboxylic acid tert-butyl ester and R-(−)-2-methylpiperindine (obtained from Advanced Asymmetrics). LCMS:

LC $R_T$=1.09 min., MS: 255 (M+H).

$^1$H NMR (300 MHz, $CDCl_3$), δ (ppm): 3.15 (m, 2H), 3.3 (m, 3H), 2.97 (m, 1H), 2.71 (m, 1H), 2.47 (m, 1H), 1.98 (m, 2H), 1.96-1.67 (m, 4H), 1.46 (s, 9H), 1.06 (d, 6.2 Hz, 3H).

Intermediate (vii)

4-(Toluene-4-sulfonyloxy)-piperidine-1-carboxylic acid tert-butyl ester

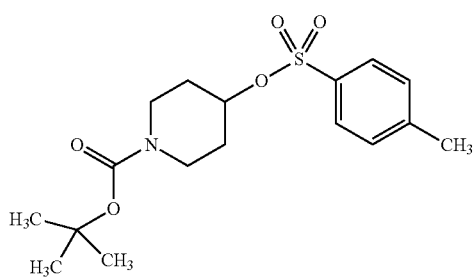 [SMILES: Cc1ccc(S(=O)(=O)OC2CCN(C(=O)OC(C)(C)C)CC2)cc1]

To a solution of p-toluenesulfonylchloride (6.42 g, 33.69 mmol) in $CH_2Cl_2$ (45 mL) and N,N-dimethylformamide (5 mL), chilled to 0° C., was added triethylamine (7.2 mL, 51.66 mmol), dimethylaminopyridine (275 mg, 2.25 mmol) and then dropwise addition of N-Boc-4-hydroxypiperidine (4.52 g, 22.46 mmol) in $CH_2Cl_2$ (45 mL). Stirred the resulting mixture for 3 days and then added 1M $H_3PO_4$ (40 mL), separated the layers and extracted with $CH_2Cl_2$ (50 mL).

Combined the organics, washed with NaHCO$_3$ (aq) (40 mL), brine (40 mL), dried over MgSO$_4$, filtered and concentrated to provide a crude solid which was purified by flash column chromatography (7 to 60% EtOAc/Heptane) to provide 6.21 g (78% yield) of the title compound as a solid.

LCMS: LC R$_T$=3.54 min.; MS (ESI): 378 (M+Na).

Intermediate (Viii)

4-((S)-2-Methyl-pyrrolidin-1-yl)-piperidine-1-carboxylic acid tert-butyl ester

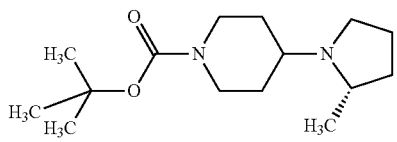

A solution of 4-(toluene-4-sulfonyloxy)-piperidine-1-carboxylic acid tert-butyl ester (8.1 g, 22.8 mmol), (S)-(+)-2-methylpyrrolidine (2.33 g, 27.36 mmol), K$_2$CO$_3$ (6.93 g, 50.16 mmol) in acetonitrile (76 mL) was heated to 80° C. for 20 h and then added additional (S)-(+)-2-methylpyrrolidine (834 mg, 9.79 mmol), and continued heating for 20 h. The heating was removed and the solution was concentrated to provide a residue which was taken up with H$_2$O (100 mL) and extracted with CH$_2$Cl$_2$ (2×100 mL). The organic layer was dried over K$_2$CO$_3$, filtered and concentrated to provide a crude oil which was purified by flash column chromatography (0 to 5% MeOH/CH$_2$Cl$_2$) to provide 2.43 g (40% yield) of the title compound as a solid.

Intermediate (ix)

(S)-3-((S)-2-Methyl-piperidin-1-yl)-pyrrolidine-1-carboxylic acid tert-butyl ester

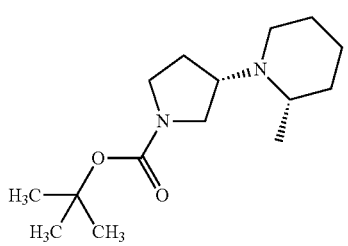 [SMILES: C[C@H]1CCCCN1[C@H]1CCN(C(=O)OC(C)(C)C)C1]

The title compound was prepared in a manner substantially the same as intermediate (iv), (2R,3'S)-2-methyl-[1,3']bipyrrolidinyl-1'-carboxylic acid tert-butyl ester, by condensing 3-(3R)-(toluene-4-sulfonyloxy)-pyrrolidine-1-carboxylic acid tert-butyl ester (5 g) with (S)-2-Methyl-piperidine to get 1.5 g (38% yield) of the product as a beige oil.

LCMS: LC R$_T$=1.95 min. MS: 269.

Intermediate (x)

(2S,3'R)-2-Methyl-[1,3']bipyrrolidinyl dihydrochloride

To a chilled solution of Intermediate (v), (2S,3'R)-2-methyl-[1,3']bipyrrolidinyl-1'-carboxylic acid tert-butyl ester, (2.51 g, 9.87 mmol) in 1,4-dioxane (9 mL) at 0° C. was added 4N HCl in dioxane (6 mL) and allowed to stir for 20 h at ambient temperature. The reaction mixture was concentrated to afford an oil which was dried under high vacuum to obtain 2.29 g of the title compound.

MS: 155 (M+H).
$^1$H NMR: (D$_2$O, 300 MHz), δ (ppm): 11.6 (bs, 1H), 9.1 (bs, 1H) 4.12 (m, 1H) 3.5, (m, 2H), 3.3-3.1 (m, 3H), 2.4-2.1 (m, 4H), 2.4 (m, 2H), 1.6 (m, 1H), 1.4 (d, 6.0 Hz, 3H).

Intermediate (xi)

(2S,3'S)-2-Methyl-[1,3']bipyrrolidinyl dihydrochloride

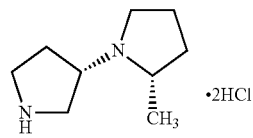

(2S,3'S)-2-Methyl-[1,3']bipyrrolidinyl-1'-carboxylic acid tert-butyl ester (24.5 g) was dissolved in 30 ml of dry 1,4-dioxane. HCl solution (85 ml, 4M in dioxane) was added at 0° C., and allowed to stir at room temperature. Brown gum appeared after about 20 minutes. After 4 h, the reaction was complete. Nitrogen was passed through the flask for 1 h with stirring. The gas outlet was passed through KOH solution to absorb HCl. The solvent was removed by vacuum to afford 29 g of hygroscopic beige gum.

LCMS: LC R$_T$=0.37 min., MS: 155 (M+H).
$^1$H NMR: (D$_2$O, 300 MHz), δ (ppm): 11.6 (bs, 1H), 9.1 (bs, 1H) 4.12 (m, 1H) 3.5, (m, 2H), 3.3-3.1 (m, 3H), 2.4-2.1 (m, 4H), 2.4 (m, 2H), 1.6 (m, 1H), 1.4 (d, 6.0 Hz, 3H)

Intermediate (xii)

(2R,3'S)-2-Methyl-[1,3']bipyrrolidinyl dihydrochloride

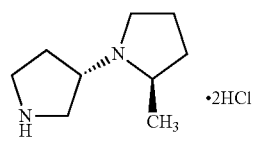

The title compound was prepared in a manner substantially the same as intermediate (x), (2S,3'R)-2-methyl-[1,3']bipyrrolidinyl dihydrochloride, by acid hydrolysis of (2R)-2-methyl-[1,3'(3'S)]bipyrrolidinyl-1'-carboxylic acid tert-butyl ester.

MS: 155 (M+H).

$^1$H NMR: (D$_2$O, 300 MHz), δ (ppm): 11.6 (bs, 1H), 9.1 (bs, 1H) 4.12 (m, 1H) 3.5, (m, 2H), 3.3-3.1 (m, 3H), 2.4-2.1 (m, 4H), 2.4 (m, 2H), 1.6 (m, 1H), 1.4 (d, 6.0 Hz, 3H).

Intermediate (xiii)

(2R,3'R)-2-Methyl-[1,3']bipyrrolidinyl dihydrochloride

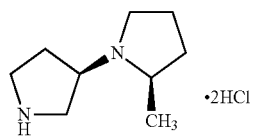

The title compound was prepared in a manner substantially the same as intermediate (x), (2S,3'R)-2-Methyl-[1,3']bipyrrolidinyl dihydrochloride, by acid hydrolysis of 2-(2R)-methyl-[1,3'(3'R)]bipyrrolidinyl-1'-carboxylic acid tert-butyl ester.

MS: 155 (M+H).

$^1$H NMR: (D$_2$O, 300 MHz), δ (ppm): 11.6 (bs, 1H), 9.1 (bs, 1H) 4.12 (m, 1H) 3.5, (m, 2H), 3.3-3.1 (m, 3H), 2.4-2.1 (m, 4H), 2.4 (m, 2H), 1.6 (m, 1H), 1.4 (d, 6.0 Hz, 3H)

Intermediate (xiv)

4-((S)-2-Methyl-pyrrolidin-1-yl)-piperidine

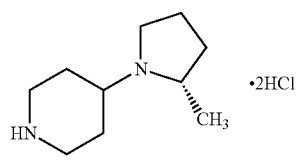

To a chilled solution of Intermediate (viii), 4-((S)-2-methyl-pyrrolidin-1-yl)-piperidine-1-carboxylic acid tert-butyl ester, (2.43 g, 9.05 mmol) in 1,4-dioxane (9 mL) at 0° C. was added 4N HCl in dioxane (6 mL) and allowed to stir for 20 h at ambient temperature. The reaction mixture was concentrated to afford an oil which was dried under high vacuum to afford 2.52 g of the title compound.

LCMS: LC R$_T$=3.6 min.; MS (ESI): m/z=169.17 (M+H)

$^1$H NMR (300 MHz CDCl$_3$) δ: 3.12 (2H, m), 2.88 (2H, m), 2.59 (4H, m), 2.02-1.59 (6H, m), 1.59-1.31 (3H, m), 1.05 (3H, d, J=6.05 Hz).

Intermediate (xv)

(2S,3'S)-2-Methyl-1'-(6-methyl-5-nitro-pyridin-2-yl)-[1,3']bipyrrolidinyl

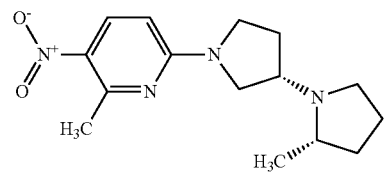

To a solution of (2S,3'S)-2-methyl-[1,3']bipyrrolidinyl dihydrochloride (0.596 g, 2.64 mmol,) in acetonitrile (25 mL) was added 2-chloro-5-nitro-6-picoline (0.685 g, 3.96 mmol,) and powdered potassium carbonate (1.45 g, 10.6 mmol), then heated to 65° C. for 4.0 hr, then at 45° C. for 16 hr. The reaction mixture was then allowed to cool to room temperature and filtered through a 10.0 g Varian Bond Elut SCX (stong cation-exchange) cartridge eluting with 50 mL of (1:1) methanol in dichloromethane, 25 mL of methanol, followed by 7N ammonia in methanol (50 mL). The filtrate was concentrated under vacuum, to afford 0.633 g (82%) of the title compound.

LC/MS: LC R$_T$=1.833 min. MS (ESI) m/z=291 (M+H$^+$)

Intermediate (xvi)

(2S,3'S)-2-Methyl-1'-(6-nitro-pyridin-3-yl)-[1,3'] bipyrrolidinyl

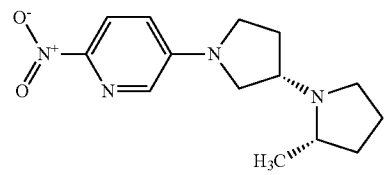 [SMILES: C[C@H]1CCCN1[C@H]1CCN(c2ccc([N+](=O)[O-])nc2)C1]

To a solution of (2S,3'S)-2-methyl-[1,3']bipyrrolidinyl dihydrochloride (0.530 g, 2.35 mmol,) in acetonitrile (25 mL) was added 5-chloro-2-nitro-pyridine (0.561 g, 3.53 mmol,) and powdered potassium carbonate (1.30 g, 9.40 mmol). The reaction mixture was then heated to 65° C. for 4.0 hr, then at 45° C. for 16 hr. The reaction mixture was then allowed to cool to room temperature and filtered through a 10.0 g Varian Bond Elut SCX (stong cation-exchange) cartridge eluting with 50 mL of (1:1) methanol in dichloromethane, 25 mL of methanol, followed by 7N ammonia in methanol (50 mL). The filtrate was concentrated under vacuum to obtain a compound which was purified again by column chromatography on silica gel eluting with methanol in dichloromethane (0-10%) to afford 0.110 g (17%) of the title compound.

LC/MS: LC R$_T$=0.899 min. MS (ESI) m/z=277 (M+H$^+$)

Intermediate (xvii)

2-methyl-6-[(3R)-3-[(2S)-2-methylpyrrolidin-1-yl]pyrrolidin-1-yl]-3-nitro-pyridine

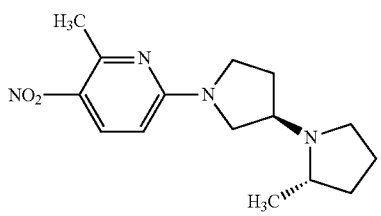 [SMILES: Cc1nc(N2CC[C@@H](N3CCC[C@@H]3C)C2)ccc1[N+](=O)[O-]]

To a solution of (2R,3'S)-2-methyl-[1,3']bipyrrolidinyl dihydrochloride (1.59 g, 7.0 mmol) in DMSO (24 mL) was added K$_2$CO$_3$ (3.87 g, 28 mmol) and 2-chloro-6-methyl-5-nitropyridine (1.81 g, 10.5 mmol) and then heated to 90° C. for 8 hours. The reaction was cooled to rt and NaHCO$_3$ (aq) (200 mL) was added. The solution was extracted with EtOAc (2×250 mL). The combined organic extracts were washed with NaHCO$_3$ (aq) (200 mL), H$_2$O (200 mL), and brine (150 mL), dried over K$_2$CO$_3$, filtered and concentrated to afford a residue which was then purified by flash column chromatography (0% to 5% MeOH/CH$_2$Cl$_2$) to afford 2 g of the title compound.

LCMS: LC R$_T$=1.68 min, MS (ESI): 291 (M+H$^+$)

$^1$H NMR (300 MHz, CDCl$_3$) δ: 8.15 (d, J=9.35 Hz, 1H), 6.21 (d, J=9.35 Hz, 1H), 3.45 (br, 5H), 2.99 (m, 1H), 2.84 (q, J=6.60 Hz, 1H), 2.55 (q, J=8.06 Hz, 1H), 2.28 (br, 1H), 1.99 (m, 2H), 1.79 (m, 2H), 1.48 (m, 1H), 1.13 (d, J=2.63 Hz, 3H)

Intermediate (xviii)

5-((2S,3'S)-2-Methyl-[1,3']bipyrrolidinyl-1'-yl)-pyridin-2-ylamine

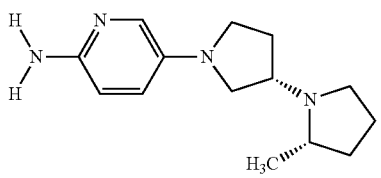

To a solution of (2S,3'S)-2-methyl-1'-(6-nitro-pyridin-3-yl)-[1,3']bipyrrolidinyl (0.110 g, 0.398 mmol) in methanol (30 mL) in a 250 mL parr bottle was added 5% Pd/C (0.030 g). The reaction mixture was allowed to shake under a hydrogen atmosphere (55 psi) at room temperature for 3 hours. The reaction mixture was filtered through a pad of Celite and the filtrate was concentrated under vacuum to afford 0.091 g (93%) of title compound.

LC/MS: LC R$_T$=0.16 min. MS (ESI) m/z=247 (M+H$^+$)

$^1$H NMR ((CDCl$_3$), 300 MHz): δ7.50 (d, J=2.93 Hz, 1H), 6.83 (dd, J=8.61, 2.93 Hz, 1H), 6.49 (d, 8.61 Hz, 1H), 3.94 (br.s., 2H), 3.51-3.12 (m, 5H), 3.05-2.95 (m, 1), 2.76 (q, J=6.96 Hz, 1H), 2.53 (q, J=8.80 Hz, 1H), 2.17-1.89 (m, 3H), 1.88-1.68 (m, 2H), 1.52-1.40 (m, 2H), 1.12 (d, J=6.05, 3H).

Intermediate (xix)

2-Methyl-6-((2S,3'S)-2-methyl-[1,3']bipyrrolidinyl-1'-yl)-pyridin-3-yl-amine

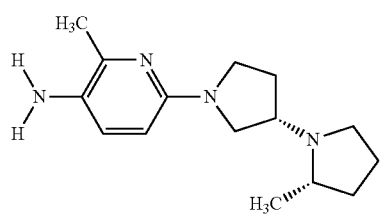 [SMILES: Cc1nc(N2CC[C@H](N3CCC[C@@H]3C)C2)ccc1N]

To a solution of (2S,3'S)-2-methyl-1'-(6-methyl-5-nitro-pyridin-2-yl)-[1,3']bipyrrolidinyl (0.633 g, 2.18 mmol) in methanol (60 mL) in a 250 mL parr shaker bottle was added 5% Pd/C (0.200 g). The reaction mixture was allowed to shake under a hydrogen atmosphere (55 psi) at room temperature for 4 hours. The reaction mixture was filtered through a pad of Celite and the filtrate was concentrated under vacuum to afford 0.544 g (96%) of title compound.

LC/MS: LC R$_T$=0.16 min. MS (ESI) m/z=261 (M+H$^+$).

$^1$H NMR ((CDCl$_3$), 300 MHz): δ6.98 (d, J=8.43 Hz, 1H), 6.19 (d, J=8.43 Hz, 1H), 3.84-3.63 (m, 4H), 3.39-3.26 (m, 2H), 3.08-2.95 (m, 1), 2.32 (s, 3H), 2.19-1.68 (m, 7H), 1.50 (br.s., 3H).

Intermediate (xx)

2-Methyl-6-[(3R)-3-[(2S)-2-methylpyrrolidin-1-yl]pyrrolidin-1-yl]pyridin-3-amine

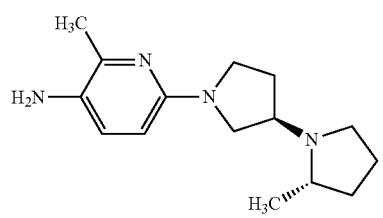 [SMILES: Cc1nc(N2CC[C@@H](N3CCC[C@@H]3C)C2)ccc1N]

A mixture of 2-methyl-6-[(3R)-3-[(2S)-2-methylpyrrolidin-1-yl]pyrrolidin-1-yl]-3-nitro-pyridine (2.0 g, 6.89 mmol) and 10% Pd/C (200 mg) in ethanol (40 mL) was shaken on a parr shaker under 50 psi H$_2$ for 18 h. The reaction mixture was filtered through a celite pad and concentrated to afford a dark red oil which was then purified by flash column chromatography (10% MeOH/CH$_2$Cl$_2$) to afford 580 mg (32% yield) of the title compound as an oil.

LC R$_T$=0.16 min, MS (ESI): 261

$^1$H NMR (300 MHz, CDCl$_3$) δ: 6.90 (d, J=8.43 Hz, 1H), 6.13 (d, J=8.43 Hz, 1H), 3.57 (m, 2H) 3.32 (m, 3H), 3.02 (m,

1H), 2.80 (m, 1H), 2.58 (m, 1H), 2.34 (s, 3H), 2.22 (m, 1H), 1.98 (m, 2H), 1.77 (m, 2H), 1.47 (m, 1H), 1.14 (d, J=6.05 Hz, 3H)

EXAMPLES

Example 1

Tetrahydro-pyran-4-carboxylic acid [2-methyl-6-((2S,3'S)-2-methyl-[1,3']bipyrrolidinyl-1'-yl)-pyridin-3-yl]-amide

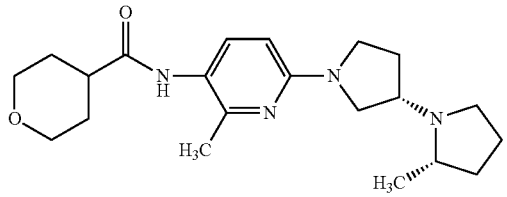 [SMILES: Cc1nc(N2CC[C@H](N3CCC[C@@H]3C)C2)ccc1NC(=O)C1CCOCC1]

To a solution of 2-methyl-6-((2S,3'S)-2-methyl-[1,3']bipyrrolidinyl-1'-yl)-pyridin-3-yl amine (0.1 g, 0.385 mmol) in DCM (3 mL) and DMF (1 mL), was added sequentially tetrahydro-2H-pyran-4-carboxlic acid (0.06 g, 0.461 mmol), N-methylmorpholine (0.127 mL, 1.16 mmol), 1-hydroxylbenzotriazole (HOBT) (0.068 g, 0.504 mmol), and EDCl.HCl (0.096 g, 0.504 mmol). The reaction mixture was stirred at room temperature for 16 hours. The reaction was quenched with a saturated aqueous solution of sodium bicarbonate (3 mL) and 15 mL of dichloromethane. The aqueous layer was extracted with dichloromethane (15 mL, 2×). The combined organic layers were washed with sodium bicarbonate (15 mL), brine (15 mL), dried over $Na_2SO_4$, and concentrated under vacuum. Purification by column chromatography on silica gel (0-10%) methanol in dichloromethane afforded 0.103 g (73%) of the title compound.

LC/MS: LC $R_T$=0.21 min. MS (ESI) m/z=373 (M+H$^+$)

$^1$H NMR ((CDCl$_3$), 300 MHz): δ7.50 (d, J=8.80, 1H), 6.87 (br.s. 1H), 6.16 (d, J=8.80 Hz, 1H), 4.10-4.01 (m, 2H), 3.80-3.71 (m, 1H), 3.66-3.56 (m, 1H), 3.50-3.17 (m, 5H), 3.05-2.97 (m, 1), 2.80 (q, J=7.51 Hz, 1H), 2.59-2.44 (m, 2H), 2.31 (s, 3H), 2.18-2.07 (m, 1H), 2.05-1.65 (m, 8H), 1.53-1.40 (m, 1H), 1.12 (d, J=6.23 Hz, 3H).

Example 2

Tetrahydro-pyran-4-carboxylic acid [5-((2S,3'S)-2-methyl-[1,3']bipyrrolidinyl-1'-yl)-pyridin-2-yl]-amide

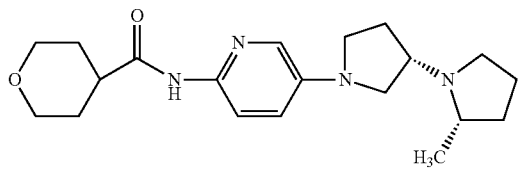 [SMILES: C[C@H]1CCCN1[C@H]1CCN(c2ccc(NC(=O)C3CCOCC3)nc2)C1]

To a solution of 5-((2S,3'S)-2-Methyl-[1,3']bipyrrolidinyl-1'-yl)-pyridin-2-ylamine (0.091 g, 0.369 mmol) in DCM (3 mL) and DMF (1 mL), was added sequentially tetrahydro-2H-pyran-4-carboxlic acid (0.058 g, 0.443 mmol), N-methylmorpholine (0.122 mL, 1.11 mmol), 1-hydroxylbenzotriazole (HOBT) (0.065 g, 0.481 mmol), and EDCl.HCl (0.092 g, 0.481 mmol). The reaction mixture was stirred at room temperature for 16 hours. The reaction was quenched with a saturated aqueous solution of sodium bicarbonate (3 mL) and 15 mL of dichloromethane. The aqueous layer was extracted with dichloromethane (15 mL, 2×). The combined organic layers were washed with sodium bicarbonate (15 mL), brine (15 mL), dried over $Na_2SO_4$, and concentrated under vacuum. Purification by column chromatography on silica gel (0-10%) methanol in dichloromethane afforded 4.7 mg (4.0%) of the title compound.

LC/MS: LC $R_T$=0.42 min. MS (ESI) m/z=359 (M+H$^+$)

$^1$H NMR ((CDCl$_3$), 300 MHz): δ8.05 (d, J=8.98 Hz, 1H), 7.69 (br.s., 1H), 7.59 (d, J=2.75 Hz, 1H), 6.89 (dd, J=7.15, 3.12 Hz, 1H), 4.10-4.01 (m, 2H), 3.74-3.69 (m, 1H), 3.54-3.16 (m, 7H), 3.06-2.96 (m, 1H), 2.79 n (q, J=7.15 Hz, 1H), 2.60-2.36 (m, 2H), 2.21-1.60 (m, 8H), 1.58-1.40 (m, 1H), 1.12 (d, j=6.23 Hz 3H).

Example 3

Naphthalene-1-carboxylic acid [2-methyl-6-((2S,3'S)-2-methyl-[1,3']bipyrrolidinyl-1'-yl)-pyridin-3-yl]-amide

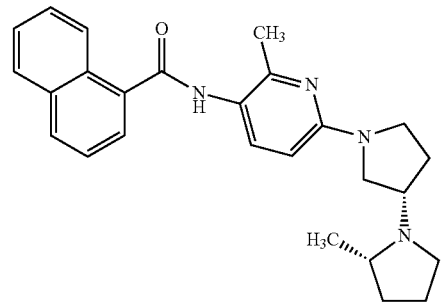 [SMILES: Cc1nc(N2CC[C@H](N3CCC[C@@H]3C)C2)ccc1NC(=O)c1cccc2ccccc12]

To a solution of 2-methyl-6-((2S,3'S)-2-methyl-[1,3']bipyrrolidinyl-1'-yl)-pyridin-3-ylamine (0.025 g, 0.096 mmol) in dichloromethane (3 mL) and pyridine (0.5 mL) was added 1-naphthoyl chloride (0.055 g, 0.288 mmol). The reaction mixture was allowed to stir for 16 hours at room temperature. The reaction mixtures were filtered through a 2.0 g Varian Bond Elut SCX (stong cation-exchange) cartridge eluting with 20 mL of methanol, followed by 7N ammonia in methanol (20 mL), and concentrated under vacuum. The crude product was purified over a silica gel column eluting with methanol in dichloromethane (0-10%) over 30 minutes to obtain 0.0247 g (62%) of the compound.

LC/MS: LC $R_T$=2.417 min. MS (ESI) m/z=415 (M+H$^+$)

$^1$H NMR ((CDCl$_3$), 300 MHz): δ8.42 (d, J=7.70 Hz, 1H), 7.96 (d, J=7.70 Hz, 1H), 7.90 (d, J=7.70 Hz, 1H), 7.82 (d, J=7.70 Hz, 1H), 7.77 (d, J=7.70 Hz, 1H), 7.63-7.47 (m, 3H), 7.29 (s, 1H), 6.27 (d, J=8.80 Hz, 1H), 3.81 (t, J=7.15 Hz, 1H), 3.66 (t, J=10.08 Hz, 1H), 3.45-3.16 (m, 3H), 3.09-2.90 (m, 1H), 2.88-2.76 (m, 1H), 2.56 (q, J=8.43 Hz, 1H), 2.44 (s, 3H), 2.22-2.09 (m, 1H), 2.05-1.92 (m, 2H), 1.88-1.65 (m, 2H), 1.56-1.41 (m, 2H), 1.14 (d, J=6.23 Hz, 3H).

Example 4

N-[2-Methyl-6-((2S,3'S)-2-methyl-[1,3']bipyrrolidinyl-1'-yl)-pyridin-3-yl]-2-phenyl-acetamide

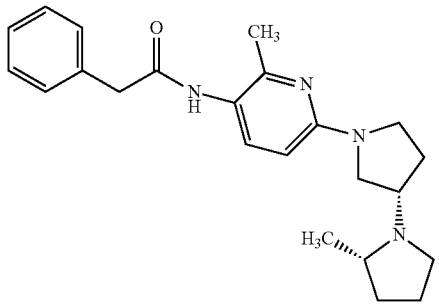 [SMILES: Cc1nc(N2CC[C@H](N3CCC[C@@H]3C)C2)ccc1NC(=O)Cc1ccccc1]

The title compound was synthesized substantially in the same manner as Example 3 by coupling of 2-methyl-6-((2S,3'S)-2-methyl-[1,3']bipyrrolidinyl-1'-yl)-pyridin-3-ylamine (0.025 g, 0.096 mmol) with phenacetyl chloride (0.045 g, 0.288 mmol) in dichloromethane (3 mL) and pyridine (0.500 mL) to obtain 0.0205 g (56%) of the title compound.

LC/MS: LC $R_T$=2.217 min. MS (ESI) m/z=379 (M+H$^+$)

$^1$H NMR ((CDCl$_3$), 300 MHz): δ7.58 (d, J=8.80 Hz, 1H), 7.46-7.33 (m, 5H), 6.61 (br.s., 1H), 6.61 (d, J=8.80 Hz, 1H), 3.75 (s, 2H), 3.63-3.53 (m, 1H), 3.38-3.11 (m, 1H), 3.05-2.94 (m, 1H), 2.79 (q, J=7.23 Hz, 1H), 2.52 (q, J=8.61 Hz, 1H), 2.08 (s, 3H), 2.04-1.88 (m, 2H), 1.86-1.60 (m, 4H), 1.53-1.39 (m, 1H), 1.11 (d, 6.23 Hz, 3H).

Example 5

Cyclohexanesulfonic acid [2-methyl-6-((2S,3'S)-2-methyl-[1,3']bipyrrolidinyl-1'-yl)-pyridin-3-yl]-amide

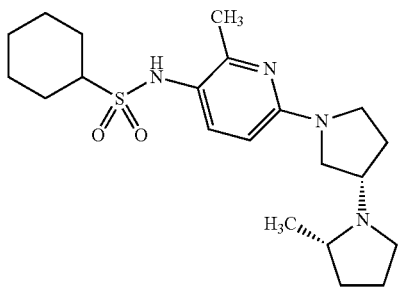 [SMILES: Cc1nc(N2CC[C@H](N3CCC[C@@H]3C)C2)ccc1NS(=O)(=O)C1CCCCC1]

The title compound was synthesized substantially in the same manner as Example 3 by coupling of 2-methyl-6-((2S,3'S)-2-methyl-[1,3']bipyrrolidinyl-1'-yl)-pyridin-3-ylamine (0.025 g, 0.096 mmol) with cyclohexanesulfonyl chloride (0.053 g, 0.288 mmol) in dichloromethane (3 mL) and pyridine (0.500 mL) to obtain 0.0195 g (50%) of the compound.

LC/MS: LC $R_T$=2.433 min. MS (ESI) m/z=407 (M+H$^+$)

$^1$H NMR ((CDCl$_3$), 300 MHz): δ7.43 (d, J=8.61 Hz, 1H), 6.17 (d, J=8.61 Hz, 1H), 5.64 (s, 1H), 3.81-3.72 (m, 1H), 3.68-3.57 (m, 1H), 3.41-3.19 (m, 3H), 3.04 (br.s., 1H), 2.96- 2.77 (m, 2H), 2.63-2.51 (m, 1H), 2.45 (s, 3H), 2.25-2.09 (m, 3H), 2.05-1.70 (m, 7H), 1.69-1.42 (m, 4H), 1.29-1.19 (m, 2H), 1.14 (d, J=5.87 Hz, 3H).

Example 6

3,4-Difluoro-N-[2-methyl-6-((2S,3'S)-2-methyl-[1,3']bipyrrolidinyl-1'-yl)-pyridin-3-yl]-benzenesulfonamide

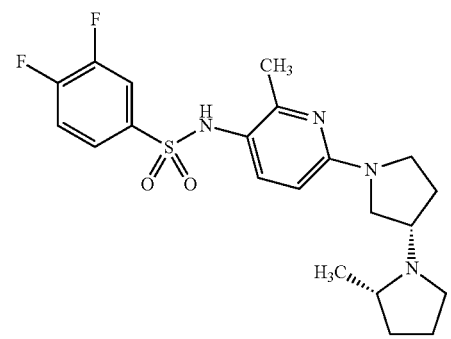 [SMILES: Cc1nc(N2CC[C@H](N3CCC[C@@H]3C)C2)ccc1NS(=O)(=O)c1ccc(F)c(F)c1]

The title compound was synthesized substantially in the same manner as Example 3 by coupling of 2-methyl-6-((2S,3'S)-2-methyl-[1,3']bipyrrolidinyl-1'-yl)-pyridin-3-ylamine (0.025 g, 0.096 mmol) with 3,4-difluorobenzenesulfonyl chloride (0.061 g, 0.288 mmol) in dichloromethane (3 mL) and pyridine (0.5 mL) to obtain 0.015 g (36%) of the title compound.

LC/MS: LC $R_T$=2.500 min. MS (ESI) m/z=437 (M+H$^+$)

$^1$H NMR ((CDCl$_3$), 300 MHz): δ7.62-7.52 (m, 1H), 7.50-7.43 (m, 1H), 7.30-7.22 (m, 1H), 7.16 (d, J=8.80 Hz, 1H), 6.10 (d, J=8.80 Hz, 1H), 3.80-3.69 (m, 1H), 3.65-3.54 (m, 1H), 3.39-3.18 (m, 3H), 3.06-2.97 (m, 1H), 2.86-2.74 (m, 1H), 2.60-2.48 (m, 1H), 2.19-2.08 (m, 1H), 2.04 (s, 3H), 2.03-1.92 (m, 1H), 1.88-1.57 (m, 3H), 1.54-1.40 (m, 1H), 1.12 (d, J=6.05 Hz, 3H).

Example 7

N-[2-Methyl-6-((2S,3'S)-2-methyl-[1,3']bipyrrolidinyl-1'-yl)-pyridin-3-yl]-benzamide

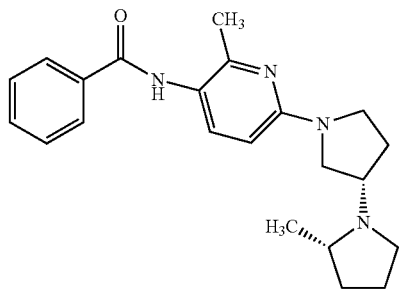 [SMILES: Cc1nc(N2CC[C@H](N3CCC[C@@H]3C)C2)ccc1NC(=O)c1ccccc1]

The title compound was synthesized substantially in the same manner as Example 3 by coupling of 2-methyl-6-((2S,3'S)-2-methyl-[1,3']bipyrrolidinyl-1'-yl)-pyridin-3-ylamine (0.025 g, 0.096 mmol) with benzoyl chloride (0.041 g, 0.288 mmol) in dichloromethane (3 mL) and pyridine (0.5 mL) to obtain 0.0084 (24% yield) of the title compound.

LC/MS: LC $R_T$=2.067 min. MS (ESI) m/z=365 (M+H$^+$)

$^1$H NMR ((CDCl$_3$), 300 MHz): δ: 7.88 (d, J=7.15 Hz, 2H), 7.71 (d, J=8.80 Hz, 1H), 7.59-7.45 (m, 3H), 7.43 (br.s., 1H), 6.24 (d, J=8.80 Hz, 1H), 3.80 (t, J=7.51 Hz, 1H), 3.65 (t, J=9.16 Hz, 1H), 3.44-3.18 (m, 3H), 3.11-2.99 (m, 1H), 2.84 (q, J=6.78 Hz, 1H), 2.57 (q, J=8.43 Hz, 1H), 2.41 (s, 3H), 2.21-2.10 (m, 1H), 2.05-1.95 (m, 2H), 1.90-1.66 (m, 2H), 1.56-1.43 (m, 1H), 1.15 (d, J=6.23 Hz, 3H).

Example 8

1-Acetyl-piperidine-4-carboxylic acid [2-methyl-6-((2S,3R)-2-methyl-[1,3']bipyrrolidinyl-1'-yl)-pyridin-3-yl]-amide

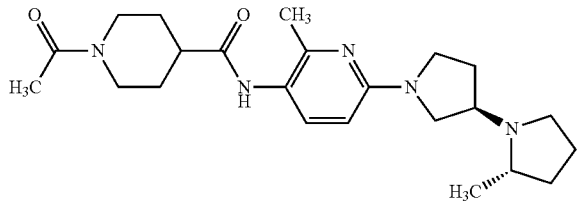

To a solution of 2-methyl-6-[(3R)-3-[(2S)-2-methylpyrrolidin-1-yl]pyrrolidin-1-yl]pyridin-3-amine (22.7 mg, 0.09 mmol) in DCE (1 mL) was added pyridine (0.22 mL, 2.7 mmol) followed by a solution of 1-acetyl-piperidine-4-carbonyl chloride (51 mg, 0.27 mmol) in DCE (1 mL) and stirred at ambient temperature for 5 hours. To this mixture was then added trisamine resin (200 mg, 0.8 mmol, 4 mmol/g loading), stirred for 30 min, filtered and concentrated to afford a crude solid which was purified by flash column chromatography (5% 7N NH$_3$ in MeOH/CH$_2$Cl$_2$) to obtain 8.89 mg of the title compound.

LC $R_T$=1.78 min, MS (ESI): 414

$^1$H NMR (300 MHz, CDCl$_3$) δ: 7.51 (d, J=8.80 Hz, 1H), 6.78 (s, 1H), 6.19 (d, J=8.80 Hz, 1H), 4.64 (d, J=13.20 Hz, 1H), 3.91 (d, J=13.56 Hz, 1H), 3.68-3.57 (m, 2H), 3.43-3.25 (m, 3H), 3.15 (td, J=14.66, 2.75 Hz, 1H), 2.99 (td, J=8.43, 3.67 Hz, 1H), 2.88-2.66 (m, 2H), 2.62-2.43 (m, 2H), 2.32 (s, 3H), 2.29-2.18 (m, 1H), 2.11 (s, 3H), 2.06-1.93 (m, 4H), 1.89-1.70 (m, 4H), 1.53-1.40 (m, 1H), 1.13 (d, J=6.23 Hz, 3H)

Example 9

5-Fluoro-2-methyl-N-[2-methyl-6-((2S,3'R)-2-methyl-[1,3']bipyrrolidinyl-1'-yl)-pyridin-3-yl]-benzamide

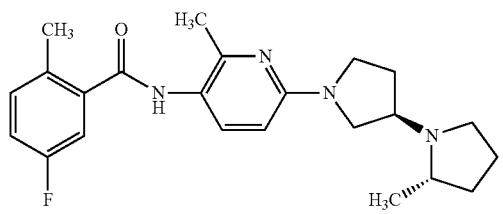 [SMILES: Cc1ccc(F)cc1C(=O)Nc1ccc(N2CC[C@@H](N3CCC[C@@H]3C)C2)nc1C]

To a solution of 2-methyl-6-[(3R)-3-[(2S)-2-methylpyrrolidin-1-yl]pyrrolidin-1-yl]pyridin-3-amine (22.7 mg, 0.09 mmol) in DCE (1 mL) was added pyridine (0.22 mL, 2.7 mmol) followed by a solution of 5-fluoro-2-methyl-benzoyl chloride (47 mg, 0.27 mmol) in DCE (1 mL) and stirred at ambient temperature for 5 hours. To this mixture was then added trisamine resin (200 mg, 0.8 mmol, 4 mmol/g loading), stirred for 30 min, filtered and concentrated to afford a crude solid which was purified by flash column chromatography (5% 7N NH$_3$ in MeOH/CH$_2$Cl$_2$) to obtain 10.4 mg of the title compound.

LC $R_T$=2.23 min, MS (ESI): 397

$^1$H NMR (300 MHz, CDCl$_3$) δ: 7.68 (d, J=8.80 Hz, 1H), 7.22 (dd, J=8.80, 2.38 Hz, 1H), 7.06 (td, J=8.43, 2.75 Hz, 1H), 7.02 (s, 1H), 6.25 (d, J=8.80 Hz, 1H), 3.71-3.60 (m, 2H), 3.45-3.26 (m, 2H), 3.00 (td, J=8.43, 3.67 Hz, 1H), 2.82 (q, J=6.23 Hz, 1H), 2.57 (q, J=8.43 Hz, 1H), 2.49 (s, 3H), 2.41 (s, 3H), 2.36-2.19 (m, 2H), 2.12-1.91 (m, 2H), 1.89-1.68 (m, 2H), 1.55-1.40 (m, 1H), 1.14 (d, J=6.23 Hz, 3H)

Example 10

Thiophene-2-carboxylic acid [2-methyl-6-((2S,3'R)-2-methyl-[1,3']bipyrrolidinyl-1'-yl)-pyridin-3-yl]-amide

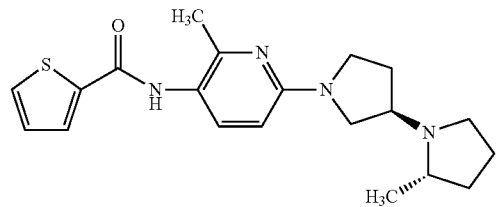 [SMILES: Cc1nc(N2CC[C@@H](N3CCC[C@@H]3C)C2)ccc1NC(=O)c1cccs1]

To a solution of 2-methyl-6-[(3R)-3-[(2S)-2-methylpyrrolidin-1-yl]pyrrolidin-1-yl]pyridin-3-amine (22.7 mg, 0.09 mmol) in DCE (1 mL) was added pyridine (0.22 mL, 2.7 mmol) followed by a solution of thiophene-2-carbonyl chloride (40 mg, 0.27 mmol) in DCE (1 mL) and stirred at ambient temperature for 5 hours. To this mixture was then added trisamine resin (200 mg, 0.8 mmol, 4 mmol/g loading), stirred for 30 min, filtered and concentrated to afford a crude solid which was purified by flash column chromatography (5% 7N NH$_3$ in MeOH/CH$_2$Cl$_2$) to obtain 7.8 mg of the title compound.

LC $R_T$=1.92 min, MS (ESI): 371

$^1$H NMR (300 MHz, CDCl$_3$) δ: 7.63 (s, 2H), 7.13 (s, 1H), 6.23 (d, J=8.25 Hz, 1H), 3.73-3.59 (m, 2H), 3.46-3.26 (m, 3H), 3.07-2.94 (m, 1H), 2.88-2.77 (m, 1H), 2.63-2.50 (m, 1H), 2.40 (s, 3H), 2.32-2.19 (m, 1H), 2.11-1.90 (m, 2H), 1.90-1.69 (m, 2H), 1.53-1.39 (m, 1H), 1.14 (s, 3H)

Example 11

3,5-Dimethyl-isoxazole-4-carboxylic acid [2-methyl-6-((2S,3'R)-2-methyl-[1,3']bipyrrolidinyl-1'-yl)-pyridin-3-yl]-amide

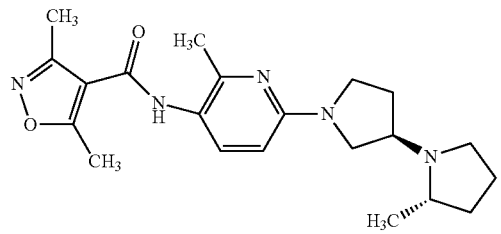 [SMILES: Cc1nc(N2CC[C@@H](N3CCC[C@@H]3C)C2)ccc1NC(=O)c1c(C)noc1C]

To a solution of 2-methyl-6-[(3R)-3-[(2S)-2-methylpyrrolidin-1-yl]pyrrolidin-1-yl]pyridin-3-amine (22.7 mg, 0.09 mmol) in DCE (1 mL) was added pyridine (0.22 mL, 2.7 mmol) followed by a solution of 3,5-dimethyl-isoxazole-4-carbonyl chloride (43 mg, 0.27 mmol) in DCE (1 mL) and stirred at ambient temperature for 5 hours. To this mixture was then added trisamine resin (200 mg, 0.8 mmol, 4 mmol/g loading), stirred for 30 min, filtered and concentrated to afford a crude solid which was purified by flash column chromatography (5% 7N NH$_3$ in MeOH/CH$_2$Cl$_2$) to obtain 12.4 mg of the title compound.

LC R$_T$=1.93 min, MS (ESI): 384

$^1$H NMR (300 MHz, CDCl$_3$) δ: 7.67 (d, J=8.80 Hz, 1H), 6.87 (s, 1H), 6.23 (d, J=8.80 Hz, 1H), 3.71-3.59 (m, 2H), 3.45-3.27 (m, 2H), 3.00 (td, J=8.80, 3.48 Hz, 1H), 2.82 (heptet, J=6.05 Hz, 1H), 2.69 (s, 3H), 2.56 (q, J=8.25 Hz, 1H), 2.52 (s, 3H), 2.39 (s, 3H), 2.31-2.16 (m, 2H), 2.09-1.90 (m, 2H), 1.89-1.67 (m, 2H), 1.53-1.40 (m, 1H), 1.14 (d, J=6.23 Hz, 3H)

Example 12

4-Fluoro-N-[2-methyl-6-((2S,3'R)-2-methyl-[1,3']bipyrrolidinyl-1'-yl)-pyridin-3-yl]-benzenesulfonamide

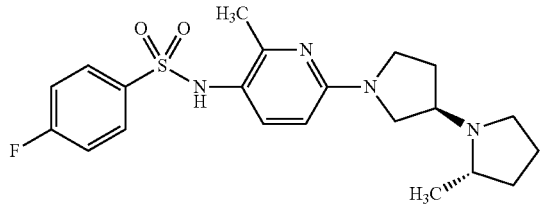 [SMILES: Cc1nc(N2CC[C@@H](N3CCC[C@@H]3C)C2)ccc1NS(=O)(=O)c1ccc(F)cc1]

To a solution of 2-methyl-6-[(3R)-3-[(2S)-2-methylpyrrolidin-1-yl]pyrrolidin-1-yl]pyridin-3-amine (22.7 mg, 0.09 mmol) in DCE (1 mL) was added pyridine (0.22 mL, 2.7 mmol) followed by a solution of 4-fluoro-benzenesulfonyl chloride (53 mg, 0.27 mmol) in DCE (1 mL) and stirred at ambient temperature for 5 hours. To this mixture was then added trisamine resin (200 mg, 0.8 mmol, 4 mmol/g loading), stirred for 30 min, filtered and concentrated to afford a crude solid which was purified by flash column chromatography (5% 7N NH$_3$ in MeOH/CH$_2$Cl$_2$) to obtain 6.9 mg of the title compound.

LC R$_T$=2.35 min, MS (ESI): 419

$^1$H NMR (300 MHz, CDCl$_3$) δ: 7.70 (dd, J=8.98, 4.95 Hz, 2H), 7.19 (d, J=8.80 Hz, 1H), 7.13 (t, J=8.43 Hz, 1H), 6.11 (d, J=8.80 Hz, 1H), 5.90 (s, 1H), 3.65-3.55 (m, 2H), 3.40-3.25 (m, 3H), 3.04-2.93 (m, 1H), 2.87-2.77 (m, 1H), 2.55 (q, J=8.61 Hz, 1H), 2.30-2.17 (m, 1H), 1.99 (s, 4H), 1.89-1.67 (m, 3H), 1.52-1.41 (m, 1H), 1.13 (d, J=6.05 Hz, 3H)

Example 13

Synthesis of Cyclopropanesulfonic acid [2-methyl-6-((2S,3'R)-2-methyl-[1,3']bipyrrolidinyl-1'-yl)-pyridin-3-yl]-amide

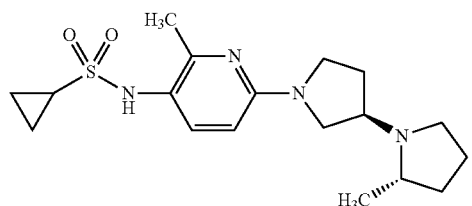

To a solution of 2-methyl-6-[(3R)-3-[(2S)-2-methylpyrrolidin-1-yl]pyrrolidin-1-yl]pyridin-3-amine (22.7 mg, 0.09 mmol) in DCE (1 mL) was added pyridine (0.22 mL, 2.7 mmol) followed by a solution of cyclopropanesulfonyl chloride (38 mg, 0.27 mmol) in DCE (1 mL) and stirred at ambient temperature for 5 hours. To this mixture was then added trisamine resin (200 mg, 0.8 mmol, 4 mmol/g loading), stirred for 30 min, filtered and concentrated to afford a crude solid which was purified by flash column chromatography (5% 7N NH$_3$ in MeOH/CH$_2$Cl$_2$) to obtain 9.7 mg of the title compound.

LC R$_T$=0.93 min, MS (ESI): 365

$^1$H NMR (300 MHz, CDCl$_3$) δ: 7.45 (d, J=8.80 Hz, 1H), 6.18 (d, J=8.80 Hz, 1H), 5.78 (s, 1H), 3.70-3.58 (m, 2H), 3.44-3.26 (m, 3H), 3.05-2.95 (m, 1H), 2.87-2.77 (m, 1H), 2.56 (q, J=8.25 Hz, 1H), 2.48 (s, 3H), 2.46-2.32 (m, 1H), 2.31-2.19 (m, 1H), 2.10-1.89 (m, 3H), 1.89-1.67 (m, 2H), 1.54-1.41 (m, 1H), 1.16-1.08 (m, 5H), 1.00-0.92 (m, 1H).

Biological Examples

Example 14

This example demonstrates the efficacy of compounds of this invention as H3 receptor ligands. The compounds of this invention have been demonstrated to displace [$^3$H]-Methylhistamine radioligand binding to mammalian cell membranes expressing rhesus (Macacca Mulatta) H3 receptor. Additionally, the compounds of this invention can also be tested by GTPγS radioligand binding assay to inhibit rhesus H3 constitutive functional activity in cell membranes. This inhibition of basal rhesus H3-mediated GTPγS radioligand binding would demonstrate that the compounds of this invention will find utility as inverse agonists. These compounds are believed to decrease rhesus H3 GTPγS radioligand binding by 0-40% below basal levels.

Rhesus H3 membranes were prepared from the Flp-In T-REx 293 Cell Line (Invitrogen) stably transfected with pcDNA5/FRT/TO (Invitrogen) containing the rhesus monkey (Macacca Mulatta) 445 amino acid H3 receptor. (Genbank #AY231164). Stably transfected cultures were amplified in tissue culture flasks by standard tissue culture methods and induced to express rhesus H3 by exposure to 500 ng/ml tetracycline (Cellgro) for 24 hours. After induction, cells were dissociated from flasks utilizing Cell Stripper (Cellgro). Cells were centrifuged (1K×g, 5 min) and pellet frozen in an ethanol-dry ice bath to disrupt cell membranes. Frozen cell pellet was re-suspended in 5 mM HEPES (pH 7.4, Invitrogen) at 10 ml/1000 cm2 of harvested cells. The cell suspension was drawn through an 18 gauge needle (2-3×) followed by a 23 gauge needle (2-3×) to further disrupt cell membranes. The cell suspension was centrifuged (40K×g, 30 min). Cell membrane pellet was re-suspended in 5 mM HEPES (pH 7.4, Invitrogen) at a final protein concentration of 10 mg/ml. Rhesus H3 membranes were stored under liquid nitrogen prior to use in [3H]-Methylhistamine and GTPγS radioligand binding assays.

Rhesus H3 radioligand binding assay was performed using rhesus H3 receptor membranes (prepared as described above), [3H]-Methylhistamine (Perkin Elmer) and WGA SPA beads (wheat germ agglutinin scintillation proximity assay) beads (Amersham). The assay was performed in 96-well Opti-Plates (Packard). Each reaction contained 50 µl rhesus H3 membranes (20-30 µg total protein), 50 µl WGA SPA beads (0.1 µg) and 50 µl of 83 Ci/mmol [$^3$H]-Methylhistamine (final concentration 2 nM) and 50 µl of tested compound. The compounds of this invention and/or vehicle were diluted with binding buffer from 10 mM DMSO stocks. Assay plates were sealed with TopSeal (Perkin Elmer) and mixed on shaker (25° C., 1 hour). Assay plates were read on TopCount scintillation counter (Packard). Results were analyzed by Hill transformation and Ki values were determined by Cheng-Prusoff equation. The observed binding data for the compounds of this invention are summarized in Table 1.

TABLE 1

| Ex. No. | Rhesus H3 Binding ki (M) |
|---|---|
| 1 | 2.40E−09 |
| 2 | 2.70E−08 |
| 3 | 4.24E−09 |
| 4 | 4.90E−09 |
| 5 | 2.63E−08 |
| 6 | 2.51E−09 |
| 7 | 8.09E−09 |
| 8 | 2.46E−09 |
| 9 | 1.95E−07 |
| 10 | 3.60E−08 |
| 11 | 8.40E−08 |
| 12 | 2.96E−08 |
| 13 | 3.71E−08 |

Example 15

This example illustrates how to study the efficacy of the compounds of this invention in increasing the wakefulness in animal models.

Male Sprague Dawley rats (Charles River, France) weighing 250±10 g are anaesthetized with ZOLETIL® 50 (60 mg/kg ip) and mounted in a stereotaxic apparatus. Cortical electrodes (small stainless steel screw electrodes of 0.9 mm in diameter) are screwed into the bone over the sensorimotor cortex (1.5 mm lateral to the median suture and 1.5 mm behind the fronto-parietal suture), the visual cortex (1.5 mm lateral to the median suture and 1.5 mm in front of the parieto-occipital suture) and over the cerebellum (reference electrode). Cortical electrodes are attached to a connector (Winchester, 7-lead) and fixed with dental cement to the cranium.

After three weeks of post-operative recovery, animals are placed in plexiglass cylinders (60 cm diameter) with free access to food and water. The temperature of the room is kept constant (21±1° C.) and lights are on from 7 a.m. to 7 p.m. The rats are recorded from 10 a.m. to 4 p.m. during three consecutive days: control day (D1), drug day (D2) and post drug day (D3). Vehicle (D1 and D3) or drug (D2) are administered 15 min before the recording.

Activity in sensorimotor and visual cortices are recorded by comparison with the reference electrode placed over the cerebellar cortex. Three stages are differentiated:

wakefulness (W) characterized by low voltage fast electrocortical (ECoG) activity;

NREM sleep (non rapid eye movement or slow wave sleep: SWS) characterized by an increase in electrocortical activity; development of high-amplitude slow waves with some bursts of sleep spindles;

REM sleep (rapid eye movement or paradoxical sleep: PS) characterized by hypersynchronization of the theta rhythm in the visual area.

Analysis of the ECoG signal is performed automatically by means of a computerized system discriminating between the various sleep phases using sequential spectral analysis of ten seconds periods (Deltamed's software "Coherence").

The compounds of this invention can be dissolved in 0.6% MTC tween and administered by oral route (po). The volume of injection is usually about 0.5 ml/100 g of body weight.

Two types of analysis can be used to quantify the effects of the compounds of this invention on sleep-wakefulness variables: the one hour-period and the six hour-period analysis.

The results are expressed in minutes (one hour-period analysis) or as the percentage of the control values (100%). Statistical analysis of the data can be carried out using the Student's t test for paired values to determine significant variations from control values.

Example 16

Stress-Induced Ultrasonic Vocalizations Test in Adult Rats

This example illustrates how to study the efficacy of the compounds of this invention as antidepressive agents in animal models.

The procedure used can be adapted from the technique described by Van Der Poel A. M, Noach E. J. K, Miczek K. A (1989) Temporal patterning of ultrasonic distress calls in the adult rat: effects of morphine and benzodiazepines. *Psychopharmacology* 97:147-8. Rats are placed for a training session in a cage with a stainless steel grid floor (MED Associates, Inc., St. Albans, Vt.). Four electric shocks (0.8 mA, 3 s) are delivered every 7 s and ultrasonic vocalizations (UV, 22 KHz) are subsequently recorded with the Ultravox system (Noldus, Wageningen, The Netherlands) during 2 min. A modified ultrasound detector (Mini-3 bat model) connected to a microphone is used to transform ultrasonic sound into audible sound. The signal is then filtered and sent to a computer where the Ultravox software recorded each bout of UV that lasted more than 10 ms. Rats are selected on the basis of their UV duration (>40 s) and subjected to the test, 4 h after training. For the test, rats are placed in the same cage as that used for training. One electric shock (0.8 mA, 3 s) is delivered and UV (duration and frequency) are subsequently recorded with the Ultravox system during 2 min. The compounds of this invention can be administered p.o. 60 min before testing.

Example 17

Forced-Swimming Test in Rats

This example further illustrates how to the study of efficacy of the compounds of this invention as antidepressive agents in animal models.

The procedure that can be used is a modification of that described by Porsolt et al. (1977) Depression: a new animal model sensitive to antidepressant treatments. Nature 266: 730-2. Rats are placed in individual glass cylinder (40 cm height, 17 cm diameter) containing water (21° C.) to a height of 30 cm. Two swimming sessions are conducted (a 15-min training session followed 24 h later by a 6-min test). After each swimming session, rats are placed under a heating lamp to avoid hypothermia. The duration of immobility is measured during the 6-min test. The compounds of this invention can be administered p.o. twice (15 min after training session and 60 min before the test).

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of formula (I):

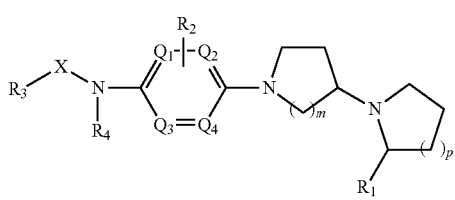

wherein:
m, p=1 or 2;
X is CO or $SO_2$;
$Q_1$ to $Q_4$ are independently CH or N provided that at least one of $Q_1$ to $Q_4$ is N;
$R_1$ is hydrogen, $(C_1-C_4)$alkyl, $CF_3$, or $(C_1-C_4)$alkoxy-$(C_1-C_4)$alkyl;
$R_2$ is hydrogen, halogen, $(C_1-C_4)$alkyl or $CF_3$;
$R_3$ is unsubstituted or substituted naphthyl, phenyl, benzyl, thiophenyl, isoxazolyl, cyclopropyl, cyclohexyl, tetrahydropyranyl or piperidinyl, wherein the substituents are selected from the group consisting of halogen, $(C_1-C_4)$alkyl and $CH_3CO$; and
$R_4$ is H or $(C_1-C_4)$alkyl;
or a salt thereof or an enantiomer or a diastereomer thereof.

2. The compound according to claim 1, wherein
m and p are 1;
X is CO;
$R_1$ is $CH_3$;
$R_2$ is $CH_3$; and
$R_3$ is unsubstituted or substituted naphthyl, phenyl, benzyl, thiophenyl, isoxazolyl, cyclopropyl, cyclohexyl, tetrahydropyranyl or piperidinyl, wherein the substituents are selected from the group consisting of halogen, $(C_1-C_4)$alkyl and $CH_3CO$; and
$R_4$ is H;
or a salt thereof or an enantiomer or a diastereomer thereof.

3. The compound according to claim 1, wherein
m and p are 1;
X is $SO_2$;
$R_1$ is $CH_3$;
$R_2$ is $CH_3$; and
$R_3$ is unsubstituted or substituted phenyl, cyclopropyl or cyclohexyl, wherein the substituents are selected from the group consisting of halogen, $(C_1-C_4)$alkyl and $CH_3CO$; and
$R_4$ is H;
or a salt thereof or an enantiomer or a diastereomer thereof.

4. The compound of claim 1 selected from the group consisting of:
tetrahydro-pyran-4-carboxylic acid [2-methyl-6-((2S,3'S)-2-methyl-[1,3']bipyrrolidinyl-1'-yl)-pyridin-3-yl]-amide;
tetrahydro-pyran-4-carboxylic acid [5-((2S,3'S)-2-methyl-[1,3']bipyrrolidinyl-1'-yl)-pyridin-2-yl]-amide;
naphthalene-1-carboxylic acid [2-methyl-6-((2S,3'S)-2-methyl-[1,3']bipyrrolidinyl-1'-yl)-pyridin-3-yl]-amide;
N-[2-methyl-6-((2S,3'S)-2-methyl-[1,3']bipyrrolidinyl-1'-yl)-pyridin-3-yl]-2-phenyl-acetamide;
cyclohexanesulfonic acid [2-methyl-6-((2S,3'S)-2-methyl-[1,3']bipyrrolidinyl-1'-yl)-pyridin-3-yl]-amide;
3,4-difluoro-N-[2-methyl-6-((2S,3'S)-2-methyl-[1,3']bipyrrolidinyl-1'-yl)-pyridin-3-yl]-benzenesulfonamide;
N-[2-methyl-6-((2S,3'S)-2-methyl-[1,3']bipyrrolidinyl-1'-yl)-pyridin-3-yl]-benzamide;
1-acetyl-piperidine-4-carboxylic acid [2-methyl-6-((2S,3'R)-2-methyl-[1,3']bipyrrolidinyl-1'-yl)-pyridin-3-yl]-amide;
5-fluoro-2-methyl-N-[2-methyl-6-((2S,3'R)-2-methyl-[1,3']bipyrrolidinyl-1'-yl)-pyridin-3-yl]-benzamide;
thiophene-2-carboxylic acid [2-methyl-6-((2S,3'R)-2-methyl-[1,3']bipyrrolidinyl-1'-yl)-pyridin-3-yl]-amide;
3,5-dimethyl-isoxazole-4-carboxylic acid [2-methyl-6-((2S,3'R)-2-methyl-[1,3']bipyrrolidinyl-1'-yl)-pyridin-3-yl]-amide;
4-fluoro-N-[2-methyl-6-((2S,3'R)-2-methyl-[1,3']bipyrrolidinyl-1'-yl)-pyridin-3-yl]-benzenesulfonamide; and
cyclopropanesulfonic acid [2-methyl-6-((2S,3'R)-2-methyl-[1,3']bipyrrolidinyl-1'-yl)-pyridin-3-yl]-amide;
or a salt thereof.

5. The compound according to claim 1 which has the formula (II):

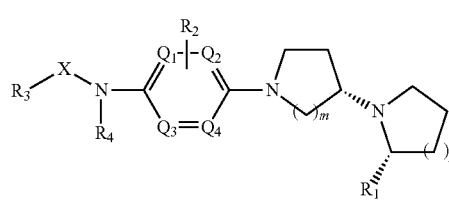

wherein $R_1$, $R_2$, $R_3$, $R_4$, $Q_1$, $Q_2$, $Q_3$, $Q_4$, X, m and p are as defined in claim 1, or a salt thereof.

6. A pharmaceutical composition comprising a compound of formula (I):

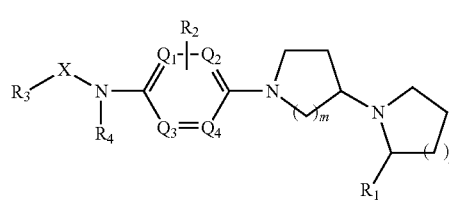

wherein:
m, p=1 or 2;
X is CO or $SO_2$;
$Q_1$ to $Q_4$ are independently CH or N provided that at least one of $Q_1$ to $Q_4$ is N;
$R_1$ is hydrogen, $(C_1-C_4)$alkyl, $CF_3$, or $(C_1-C_4)$alkoxy-$(C_1-C_4)$alkyl;
$R_2$ is hydrogen, halogen, $(C_1-C_4)$alkyl or $CF_3$;
$R_3$ is unsubstituted or substituted naphthyl, phenyl, benzyl, thiophenyl, isoxazolyl, cyclopropyl, cyclohexyl, tetrahydropyranyl or piperidinyl, wherein the substituents are selected from the group consisting of halogen, $(C_1-C_4)$alkyl and $CH_3CO$; and
$R_4$ is H or $(C_1-C_4)$alkyl; or
a pharmaceutically acceptable salt thereof or an enantiomer or a diastereomer thereof in combination with at least one pharmaceutically acceptable excipient, diluent or a carrier.

7. The composition according to claim 6, wherein the compound is selected from the group consisting of:

tetrahydro-pyran-4-carboxylic acid [2-methyl-6-((2S,3'S)-2-methyl-[1,3']bipyrrolidinyl-1'-yl)-pyridin-3-yl]-amide;

tetrahydro-pyran-4-carboxylic acid [5-((2S,3'S)-2-methyl-[1,3']bipyrrolidinyl-1'-yl)-pyridin-2-yl]-amide;

naphthalene-1-carboxylic acid [2-methyl-6-((2S,3'S)-2-methyl-[1,3']bipyrrolidinyl-1'-yl)-pyridin-3-yl]-amide;

N-[2-methyl-6-((2S,3'S)-2-methyl-[1,3']bipyrrolidinyl-1'-yl)-pyridin-3-yl]-2-phenyl-acetamide;

cyclohexanesulfonic acid [2-methyl-6-((2S,3'S)-2-methyl-[1,3']bipyrrolidinyl-1'-yl)-pyridin-3-yl]-amide;

3,4-difluoro-N-[2-methyl-6-((2S,3'S)-2-methyl-[1,3']bipyrrolidinyl-1'-yl)-pyridin-3-yl]-benzenesulfonamide;

N-[2-methyl-6-((2S,3'S)-2-methyl-[1,3']bipyrrolidinyl-1'-yl)-pyridin-3-yl]-benzamide;

1-acetyl-piperidine-4-carboxylic acid [2-methyl-6-((2S,3'R)-2-methyl-[1,3']bipyrrolidinyl-1'-yl)-pyridin-3-yl]-amide;

5-fluoro-2-methyl-N-[2-methyl-6-((2S,3'R)-2-methyl-[1,3']bipyrrolidinyl-1'-yl)-pyridin-3-yl]-benzamide;

thiophene-2-carboxylic acid [2-methyl-6-((2S,3'R)-2-methyl-[1,3']bipyrrolidinyl-1'-yl)-pyridin-3-yl]-amide;

3,5-dimethyl-isoxazole-4-carboxylic acid [2-methyl-6-((2S,3'R)-2-methyl-[1,3']bipyrrolidinyl-1'-yl)-pyridin-3-yl]-amide;

4-fluoro-N-[2-methyl-6-((2S,3'R)-2-methyl-[1,3']bipyrrolidinyl-1'-yl)-pyridin-3-yl]-benzenesulfonamide; and cyclopropanesulfonic acid [2-methyl-6-((2S,3'R)-2-methyl-[1,3']bipyrrolidinyl-1'-yl)-pyridin-3-yl]-amide; or a pharmaceutically acceptable salt thereof.

8. The composition according to claim 6, wherein the compound is having the formula (II):

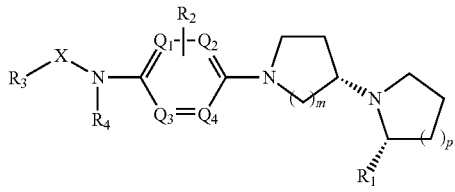

(II)

wherein $R_1$, $R_2$, $R_3$, $R_4$, $Q_1$, $Q_2$, $Q_3$, $Q_4$, X, m and p are as defined in claim 6, or a pharmaceutically acceptable salt thereof.

9. A method of treating a disease in a patient, said disease selected from the group consisting of cognitive impairment associated with schizophrenia (CIAS), anxiety disorders, generalized anxiety, panic disorder and post-traumatic stress disorder, major depressive disorder, dementia of Alzheimer type (DAT), cognitive deficits related to neurological diseases chosen from Alzheimer, Parkinson or Huntington, age related cognitive impairment, mild cognitive impairment, vascular dementia, Lewis Body dementia, cognition associated with cognitive deficits, sleep related disorders, attention deficit hyperactivity disorder and depression, and obesity, comprising administering to said patient a therapeutically effective amount of a compound of formula (I):

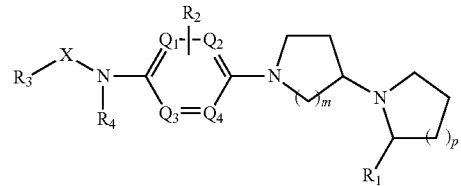

(I)

wherein:

m, p=1 or 2;

X is CO or $SO_2$;

$Q_1$ to $Q_4$ are independently CH or N provided that at least one of $Q_1$ to $Q_4$ is N;

$R_1$ is hydrogen, $(C_1-C_4)$alkyl, $CF_3$, $(C_1-C_4)$alkoxy-$(C_1-C_4)$alkyl;

$R_2$ is hydrogen, halogen, $(C_1-C_4)$alkyl or $CF_3$;

$R_3$ is unsubstituted or substituted naphthyl, phenyl, benzyl, thiophenyl, isoxazolyl, cyclopropyl, cyclohexyl, tetrahydropyranyl or piperidinyl, wherein the substituents are selected from the group consisting of halogen, $(C_1-C_4)$alkyl and $CH_3CO$; and $R_4$ is H or $(C_1-C_4)$alkyl; or a pharmaceutically acceptable salt thereof or an enantiomer or a diastereomer thereof optionally in combination with one or more pharmaceutically acceptable excipient, diluent or a carrier.

10. The method according to claim 9, wherein the sleep disorder is selected from the group consisting of narcolepsy, circadian rhythm sleep disorder, obstructive sleep apnea, periodic limb movement and restless leg syndrome, excessive sleepiness and drowsiness due to medication side-effect.

11. The method according to claim 10, wherein the sleep disorder is narcolepsy.

12. The method according to claim 9, wherein the disease is cognitive impairment associated with schizophrenia (CIAS).

13. The method according to claim 9, wherein the disease is dementia of Alzheimer type (DAT).

14. The method according to claim 9, wherein the compound is selected from the group consisting of:

tetrahydro-pyran-4-carboxylic acid [2-methyl-6-((2S,3'S)-2-methyl-[1,3']bipyrrolidinyl-1'-yl)-pyridin-3-yl]-amide;

tetrahydro-pyran-4-carboxylic acid [5-((2S,3'S)-2-methyl-[1,3']bipyrrolidinyl-1'-yl)-pyridin-2-yl]-amide;

naphthalene-1-carboxylic acid [2-methyl-6-((2S,3'S)-2-methyl-[1,3']bipyrrolidinyl-1'-yl)-pyridin-3-yl]-amide;

N-[2-methyl-6-((2S,3'S)-2-methyl-[1,3']bipyrrolidinyl-1'-yl)-pyridin-3-yl]-2-phenyl-acetamide;

cyclohexanesulfonic acid [2-methyl-6-((2S,3'S)-2-methyl-[1,3']bipyrrolidinyl-1'-yl)-pyridin-3-yl]-amide;

3,4-difluoro-N-[2-methyl-6-((2S,3'S)-2-methyl-[1,3']bipyrrolidinyl-1'-yl)-pyridin-3-yl]-benzenesulfonamide;

N-[2-methyl-6-((2S,3'S)-2-methyl-[1,3']bipyrrolidinyl-1'-yl)-pyridin-3-yl]-benzamide;

1-acetyl-piperidine-4-carboxylic acid [2-methyl-6-((2S,3'R)-2-methyl-[1,3']bipyrrolidinyl-1'-yl)-pyridin-3-yl]-amide;

5-fluoro-2-methyl-N-[2-methyl-6-((2S,3'R)-2-methyl-[1,3']bipyrrolidinyl-1'-yl)-pyridin-3-yl]-benzamide;

thiophene-2-carboxylic acid [2-methyl-6-((2S,3'R)-2-methyl-[1,3']bipyrrolidinyl-1'-yl)-pyridin-3-yl]-amide;

3,5-dimethyl-isoxazole-4-carboxylic acid [2-methyl-6-((2S,3'R)-2-methyl-[1,3']bipyrrolidinyl-1'-yl)-pyridin-3-yl]-amide;

4-fluoro-N-[2-methyl-6-((2S,3'R)-2-methyl-[1,3']bipyrrolidinyl-1'-yl)-pyridin-3-yl]-benzenesulfonamide; and cyclopropanesulfonic acid [2-methyl-6-((2S,3'R)-2-methyl-[1,3']bipyrrolidinyl-1'-yl)-pyridin-3-yl]-amide; or a pharmaceutically acceptable salt thereof.

15. The method according to claim 9, wherein the compound is having the formula (II):

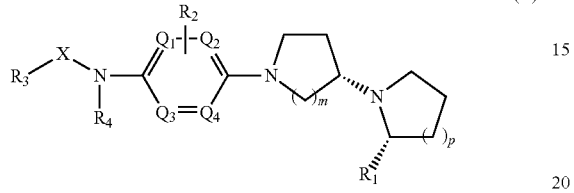

wherein $R_1$, $R_2$, $R_3$, $R_4$, $Q_1$, $Q_2$, $Q_3$, $Q_4$, X, m and p are as defined in claim 9, or a pharmaceutically acceptable salt thereof.

* * * * *